United States Patent [19]
Thompson et al.

[11] Patent Number: 6,117,677
[45] Date of Patent: *Sep. 12, 2000

[54] PLANT STEAROYL-ACP DESATURASES GENES

[76] Inventors: Gregory A. Thompson, 5127 Cowell Blvd., Davis, Calif. 95616; Vic C. Knauf, 1013 Hillview La., Winters, Calif. 95695

[*] Notice: This patent is subject to a terminal disclaimer.

[21] Appl. No.: 07/979,461

[22] Filed: Nov. 20, 1992

Related U.S. Application Data

[63] Continuation of application No. 07/494,106, Mar. 16, 1990, abandoned.

[51] Int. Cl.$^7$ .............................. C12Q 1/68; C12N 15/52; C12N 15/82; C12N 15/00

[52] U.S. Cl. .............................. 435/410; 435/6; 435/183; 435/320.1; 435/468; 536/23.1; 536/23.2; 536/23.6; 536/24.5; 800/281; 800/285; 800/298; 800/306

[58] Field of Search .............................. 435/172.3, 240.4, 435/320.1, 6, 183, 410, 419, 468; 800/205, DIG. 69, 281, 285, 306, 298; 935/64; 536/23.1, 23.6, 24.5, 23.2

[56] References Cited

U.S. PATENT DOCUMENTS

| | | | |
|---|---|---|---|
| 4,394,443 | 7/1983 | Weissman et al. | 435/6 |
| 4,446,235 | 5/1984 | Seeburg | 435/91 |
| 5,057,419 | 10/1991 | Martin et al. | 435/134 |
| 5,107,065 | 4/1992 | Shewmaker et al. | 800/205 |

FOREIGN PATENT DOCUMENTS

| | | |
|---|---|---|
| 0 189 707 | 8/1986 | European Pat. Off. ........ C12N 15/00 |
| 0 255 378 | 2/1988 | European Pat. Off. . |
| 0255377 | 2/1988 | European Pat. Off. . |
| 0323 753 | 7/1989 | European Pat. Off. . |
| 8800794 | 11/1988 | Netherlands . |
| WO 90/12084 | 10/1990 | WIPO . |
| WO 91/11906 | 8/1991 | WIPO . |
| WO 91/18985 | 12/1991 | WIPO . |

OTHER PUBLICATIONS

McKeon and Stumpf, Purification and Characterization of the Stearoyl–acyl Carrier Protein Desaturase and the Acyl–acyl Carrier Protein Thioesterase from Maturing Seeds of Safflower, *Jour. Bio. Chem.* (1982) 257:12141–12147.

McKeon and Stumpf, "Stearoyl–Acyl Carrier Protein Desaturase from Safflower Seeds," *Methods in Enzymology* (1981) 71:275–281.

Rock, et al., "Preparative Enzymatic Synthesis of Acyl–Acyl Carrier Protein," *Methods in Enzymology* (1981) 72:397–403.

Jaworsky and Stumpf, "Fat Metabolsim in Higher Plants: Properties of a Soluble Stearyl–Acyl Carrier Protein Desaturase from Maturing *Carthamus tinctorius*, " *Archives of Biochem. and Biophys.* (1974) 162:158–165.

Johnson and Gurr, "Isotope Effects in the Desaturation of Stearic to Oleic Acid," *Lipids* (1971) 6(2):78–84.

Talamo and Bloch, "A New Assay for Fatty Acid Desaturation," *Analyt. Biochem.* (1969) 29:300–304.

Nagi and Bloch, "Enzymatic Desaturation of Stearyl Acyl Carrier Protein," *Jour. Biol. Chem.* (1966) 241:1925–1927.

Inkpen and Quackenbush, "Desaturation of Palmitate and Stearate by Cell–Free Fractions From Soybean Cotyledons," *Lipids* (1968) 4(6):539–543.

Graef, et al., "Inheritance of Three Stearic Acid Mutants of Soybean", *Crop Science* (1985) 25:1076–1079.

Bafor, et al., "Properties of the Glycerol Acylating Enzymes in Microsomal Preparations from the Developing Seeds of Safflower (*Carthamus tinctorius*) and Turnip Rape (*Brassica campestris*) and their Ability to Assemble Cocoa–Butter Type Fats", *JAOCS* (1990) 67(4):217–225.

Goodman, et al., "Biotechnology and Its Impact on Future Developments In Soybean Production and Use", World Soybean Research Conference III: Proceedings (Westview Press): Shibles (ed): (1985) pp. 261–271.

Mattson, et al., "Comparison of effects of dietary saturated, mono–unsaturated, and polyunsaturated fatty acids on plasma lipids and lipoproteins in man", *J. of Lipid Research* (1985) 26:194–201.

Battey, et al., "Genetic engineering for plant oils: potential and limitations", *Trends in Biotech.* (1989) 7:122–126.

Downey, et al., "Genetic Control of Fatty Acid Composition In Oilseed Crops", Proceedings of the Flax Institute USA: 41(3):1–3 (1971).

Wilcox, et al., "Genetic Alteration of Soybean Oil Composition by a Chemical Mutagen," *JAOCS* (1984) 61:97–100.

Wolf, et al., "Effect of Temperature on Soybean Seed Constituents: Oil, Protein, Moisture, Fatty Acids, Amino Acids and Sugars", *JAOCS* (1982) 59:230–232.

Moore, et al., "The Inheritance of High Oleic Acid in Peanut", *Journal of Heredity* (1989) 80(3):252–253.

Bodman, et al., "Processing of Edible Soybean Oil", Soybeans an Soybean Products, Interscience Publishers, Inc., NY (1951) pp. 649–725.

Carver, et al., "Developmental Changes in Acyl–Compositions of Soybean Seed Selected for High Oleic Acid Concentration", *Crop Science* (1984) 24:1016–1019.

Thompson, et al., "Primary Structures of the Precursor and Mature Forms of Stearoylacyl Carrier Protein Desaturase From Safflower Embryos and Requirement of Ferredoxin for Enzyme Activity", *Proc. Natl. Acad. Sci. USA* (1991) 99:2579–2582.

(List continued on next page.)

*Primary Examiner*—John L. LeGuyader

[57] ABSTRACT

The present invention relates to DNA constructs comprising a plant stearoyl-ACP desaturase and a second DNA sequence which is not naturally joined to the given plant stearoyl-ACP desaturase. The plant stearoyl-ACP desaturase is under the regulatory control of a transcription and translation initiation region preferentially expressed in plant embryo tissue.

The amino acid sequence and methods to purify safflower stearoyl-ACP desaturase to homogenity are also provided.

30 Claims, 32 Drawing Sheets

OTHER PUBLICATIONS

Knauf, et al., "Reprogramming Levels of Fatty Acid Synthesis Enzymes in Developing Embryos of Rapeseed", *J. of Cellular Biochem.*, UCLA Symposia, Suppl. 14E (1990) Abstract R018.

Kater, et al., "Purification and Cloning of *Brassica napus* Stearoyl–ACP Desaturase," *J. Cell. Biochem. Suppl.* (1991) 15A:133.

Knauf, et al., "Reprogramming Levels of Fatty Acid Synthesis Enzymes in Developing Embryos of Rapeseed," *J. Cell. Biochem. Suppl.* (1990) 14E:266.

Chesebrough, Thomas M., "Changes in the Enzymes for Fatty Acid Synthesis and Desaturation during Acclimation of Developing Soybean Seeds to Altered Growth Temperature," *Plant Physiol.* (1989) 90:760–764.

Browse, et al., "A Mutant of Arabidopsis Deficient in C18:3 and C:16:3 Leaf Lipids," *Chem. Abstracts* (1986) 105:449 No. 105:169077c.

Hames et al 1990 Gel Electrophoresis of Proteins:Apractical Approach; 2nd Edition; IRL Press; p. 132.

Knauf 1987 Trends in Biotech 5:40–47.

Thompson et al 1991 Proc Natl Acad Sci USA 88:2578–2582.

```
              S                      S                W                   H
ASTLGSSTPKVDNAKKPFQPPREVHVQVTH  MPPQKIEIFKSIEG  AEQNILV  LKPVEKCWQ
                              X                R       F
       S
F2:  DFLPDPA  EGFDEQVKELRARAKEIPDDYFVVLVGDMITEEALPTYQTMLNTLDGV
       T
F3:  DETGASLTPWAVWT

F4:  DLLHTYLYLSGRV

F5:  DMRQIQKTIQYLI

F6:  TENSPYLGFIYTSFQER
        K             C                                      S
F7:  DV   LAQI  GTIASDEKRHETAYTKIVEKLFEIDPDGTVLAFADMRKKI  MPAHLMY
        F        Q                                       T

F8:  DNLF
             A       G
F9:  dvF1AV   QRL   VYTAK
             I     I

F10: DYADILEFLVGRWK
                              Q
F11: VADLTGLSGEGRKAQA  DYVCGLPPRIRRLEERAQGRAKEGPVVPFSWIFDRQVKL
                      G
```

FIGURE 1

```
                                                                                   HindIII
  1   GCTCACTTGTGTGGTGGAGGAGAAAAAACAGAACTCACAAAAAGCTTTGCGACTGCCAAGAACAACAACA
 69

70   ACAACAAGATCAAGAAGAAGAAGAAGATCAAAAATGGCTCTTCGAATCACTCCAGTGACCTTGCAA
138                                         METAlaLeuArgIleThrProValThrLeuGln
                                            42

EcoRV                                       BglII            NcoI
139   TCGGAGAGATATCGTTCGTTTCGTTTCCTAAGAAGGCTAATCTCCCAAATTCGCCATGGCC
207   SerGluArgTyrArgSerPheSerPhePheLysLysAlaAsnLeuArgSerProLysPheAlaMETAla
      149                                                                    201

HindII
208   TCCACCCTCGGATCATCCCAAGAAGGTTGACAATGCCAAGAAGCCTTTTCAACCTCCACGAGAGGTT
276   SerThrLeuGlySerSerThrProLysValAspAsnAlaAlaLysLysProPheGlnProProArgGluVal
                                                                            238

277   CATGTTCAGGTGACGCACTCCATGCCACCACAGAAGATAGAGATTTTCAAATCCATCGAGGGTTGGGCT
345   HisValGlnValThrHisSerMETProProGlnLysIleGluIlePheLysSerIleGluGlyTrpAla
```

FIGURE 2
Page 1 of 7

346 GAGCAGAACATATTGGTTCACCTAAAGCCAGTGGAGAAATGTTGGCAAGCACAGGATTCTTGCCGGAC
414 GluGlnAsnIleLeuValHisLeuLysProValGluLysCysTrpGlnAlaGlnAspPheLeuProAsp

FIGURE 2
Page 2 of 7

```
415  CCTGCATCTGAAGGATTTGATGAACAAGTCAAGGAACTAAGGGCAAGAGCAAAGGAGATTCCTGATGAT
483  ProAlaSerGluGlyPheAspGluGlnValLysGluLeuArgAlaArgAlaLysGluIleProAspAsp

484  TACTTTGTTGTTGTTTGGTTGGAGATATGATTACAGAGGAAGCCCTACTTACCAAACAATGCTTAAT
552  TyrPheValValValValGlyAspMETIleThrGluGluAlaLeuProThrTyrGlnThrMETLeuAsn

553  ACCCCTAGATGGTGTACGTGATGAGACTGGGGCTAGCCCTTACGCCTGTCTGGACTAGGGCTTGG
621  ThrLeuAspGlyValArgAspGluThrGlyAlaSerLeuThrProTrpAlaValTrpThrArgAlaTrp
                                                                    PvuII     AccI
622  ACAGCTGAAGAGAACAGGCATGGGCGATCTTCTCCACACCTATCTCTACCTTTCTGGGCGGGTAGACATG
690  ThrAlaGluGluAsnArgHisGlyAspLeuLeuHisThrTyrLeuTyrLeuSerGlyArgValAspMET
                                                                            684
                                                        BamHI
691  AGGCAGATACAGAAGACAATTCAGTATCTCATTGGGTCAGGAATGGATCCTCGTACCGAAAACAGCCCC
759  ArgGlnIleGlnLysThrIleGlnTyrLeuIleGlySerGlyMETAspProArgThrGluAsnSerPro
                                                                            736
```

FIGURE 2
Page 3 of 7

760 TACCTTGGGGTTCATCTACACATCGTTCAAGAGCGTGCCACATTTGTTTCTCACGGAAACACCGCCAGG
828    TyrLeuGlyPheIleTyrThrSerPheGlnGluArgAlaThrPheValSerHisGlyAsnThrAlaArg

FIGURE 2
Page 4 of 7

```
                    SphI
                     |
 829  CATGCAAAGGATCATGGGGACGTGAAACTGGCGCCAAATTTGTGGTACAATCGCGTCTGACGAAAAGCGT
 897  HisAlaLysAspHisGlyThrValLysLeuAlaAlaGlnIleCysGlyThrIleAlaSerAspGluLysArg
                                  833

ClaI
                                                      |
 898  CACGAGACCGCTTATACAAAGATAGTCGAAAAGCTATTCGAGATCGATCCTGATGGCACCGTTCTTGCT
 966  HisGluThrAlaTyrThrLysIleValGluLysLeuPheGluIleAspProAspGlyThrValLeuAla
                                                               942

BglII
                                                 |
 967  TTTGCCGACACATGATGATGAGGAAAAAGATCTCGATGCCCGCACACTTGATGTACGATGGGCGTGATGACAAC
1035  PheAlaAspMETMETArgLysLysIleSerMETProAlaHisLeuMETTyrAspGlyArgAspAspAsn
                                                 990

AccI
                                                            |
1036  CTCTTCGAACATTTCTCGGGGTTGCCCAAAGACTCGGGCGTCTACACCGCCAAAGACTACGCCGACATA
1104  LeuPheGluHisPheSerAlaValAlaAlaGlnArgLeuGlyValTyrThrAlaLysAspTyrAlaAspIle
                                                           1077
```

FIGURE 2
Page 5 of 7

1105 CTGGAATTTCTGGTCGGGCGGTGGAAAGTGGCGGATTTGACCGGCCTATCTGGTGAAGGGCGTAAAGCG
1173     LeuGluPheLeuValGlyArgTrpLysValAlaAspLeuThrGlyLeuSerGlyGluGlyArgLysAla

FIGURE 2
Page 6 of 7

```
                                                                        SacI
1174  CAAGATTATGTTTGCGGGTTGCCACCAAGAATCAGAAGGCTGGAGGAGAGAGCTCAAGGGCGAGCAAAG
1242  GlnAspTyrValCysGlyLeuProProArgIleArgArgLeuGluGluArgAlaGlnGlyArgAlaLys
                                                                       1228

PvuII
1243  GAAGGACCTGTTGTTCCATTCAGCTGGATTTTCGATAGACAGGTGAAGCTGTGAAGAAAAAAAACGA
1311  GluGlyProValValProPheSerTrpIlePheAspArgGlnValLysLeu
                                                      1266

1312  GCAGTGAGTTCGGTTTCTGTTGGCTTATTGGGTAGAGGTTAAAACCTATTTTAGATGTCTGTTTCGTGT
1380

1381  AATGTGGTTTTTTTCTTCTAATCTTGAATCTCGGTATTGTCTGTTGAGTTCGCGTGTGTGTAAACTTG
1449

1450  TGTGGCTGTGTGGACATATTATAGAACTCGTTATGCCAATTTTGATGACGGTGGTTATCGTCTCCCCTGGT
1518

1519  GTTTTTTTATTGTTT 1533
```

FIGURE 2
Page 7 of 7

Amino Acid
Sequence From
Fragment F2

```
              K   E   I   P   D   D   Y  FVVLVGDMITEEALPTY  Q   T   M   L   N   T
              AAA GAA AUU CCN GAU GAU UAU                   CAA ACN AUG CUN AAU AC/N
                G   G   C       C   C                        G               C
                            A

5'GCTAAGCTT AAP GAP ATQ CA GAQ GAQ TA3'   Desat 13-1         Forward Primers:
                    A CCG                 Desat 13-2
                      CCC                 Desat 13-3
                      CCT                 Desat 13-4

Reverse Primers:
                                          (complements)

3' GTQ TGN TAC GAN TTP TGCTTAAGCGA 5'
                                                       AAQ
                              Desat 13-5a
                              Desat 13-6a
```

Oligonucleotides

```
  1 ATGATTACCTGAAAATAAGTATAATTTGTATTGAAATTGACATTTTTTGTGTAACAAATATT        69
 70 TTGTGTAACAAGAATTAAAAAAAAACAGAAAATAACTCAGCTTTTTAATATAAAAAAATTAATTG    138
139 AGTTAGAAAATTGTTGTACCAATAACAAAAGATTTATATGGAATTATAAAATCAACACCAATAACAC  207
208 AAGACTTTTTAAAAATTTAAGAATAATAAGCAATAACAATAGAATCTTCAAATTCTTCAAATCCTTA  276
277 AAAATCAATCTCCCACTATTAATCCCCTAGTTTTAGTTGGTAATGGCAACGTTTGTTGACTACCGTA  345
346 TTGTAACTTTTGTCAAATTGTCATAAATACGTGTCAAACTCTGTAAAAAATTAGTCTGCTACATCGT  414
415 CTTTTATTTATAAAACACAGCTGTTAATCAGAATTTGGTTTATTAAATCAACAACCTGCACGAAACTTG 483
484 TGTGAGCATATTTGTCTGTTTCTGGTTCATGACCTTCTTCCGCATGATGGCCAAGTGTAATGGCCACT  552
                                                                  BglII
                                                                  |
553 TGCAAGAGCGTTCTTCAACGAGATAAGTCGAACAAATATTTGTCCGTTACGACCACATATAANATCTC  621
                                                             616
622 CCCATCTCTATATAATACCAGCATTCACCATCATGAATACCTCAAATCTCCAATCTCACAAATACTTC  690
691 AATAAAAAGACCAAAAAAATTAAAGCAAAAAAAGCCTTCTTGTGCACAAAAAAAAAGAAGCCTTCT    759
760 AGGTTTTCACGACATGAAGTTCACTACTCTAATGGTCATCACATTGGTGATAATCGCCATCTCGTCTCC  828
                         METLysPheThrThrLeuMETValIleThrLeuValIleAlaIleSerSerPr
829 TGTTCCAATTAGAGCAACCGTTGAAAGTTTCGGAGAAGTTGCACAATCGTGTTGTGACAGAACT      897
    oValProIleArgAlaThrThrValGluSerPheGlyGluValAlaGlnSerCysValValThrGluLe
```

FIGURE 5
Page 1 of 3

```
 898 CGCCCCATGCTTACCAGCAATGACCACGGCAGGAGACCCGACTACAGAATGCTGCGACAAACTGGTAGA  966
     uAlaProCysLeuProAlaMETThrThrAlaGlyAspProThrThrGluCysCysAspLysLeuValGl

967 GCAGAAACCATGTCTTTGTGGTTATATTCGAAACCCAGCTGCTTGTGACGTATGTTACTTCTCCAAACGG 1035
     uGlnLysProCysLeuCysGlyTyrIleArgAsnProAlaTyrSerMETTyrValThrSerProAsnGl

1036 TCGCAAAGTCTTAGATTTTTGTAAGGTTCCTTTTCCTAGTTGTTAAATCTCTCAAGACATTGCTAAGAA 1104
     yArgLysValLeuAspPheCysLysValProPheProSerCys .
                                                                  HindII
                                          BglII                     |
1105 AAATATTATTAAAAATAAAAGAATCAAACTAGATCTGATGTAACAATGAATCATCATGTTATGGTTGAA 1173
                                          1136                     1173

1174 GCTTATATAGCTGAAGTGTTTTGATTTTATATATTTGTGTGTGTCCTGCTCAATTTTGAAACAC 1242

1243 ACACGTTTCTCCCTGATTTGGATTTAAAATTATATTTGAGTTAAAAAAAAGAATGGAATGCTATT 1311
                                     EcoRV
                                       |
1312 TATACAAGTTGATGAAAAAGTGGAAGTACAATTTAGATATCTCCWCACTTAAAGAATGAAACAATAAT 1380
                                      1350
                                      SalI
                                        |
1381 AGACTTCGAAACAAATGAAAAATACATAAATTGTGACAATCAACGTCGATCGACGAGTTTATTATTAA 1449
                                      1414

1450 AAATTTGTGTGAAGGACTAGCAGTTCAACCAAATGATATTGAACATATACATCAACAAATATGATAATC 1518
```

FIGURE 5
Page 2 of 3

```
1519  ATAAAAGAGAGAATGGGGGGGTGTCGTTTACCAGAAACCCTCTTTTTCTCAGCTCGCTAAAACCCTA  1587
1588  CCACTAGAGACCTAGCTCTGACCGTTCGGCTCATCGGTGCCGGAGGTGTAACCTTTCTTCCCATGACCC  1656
1657  GAAACCTCTCTTCCCAACTCACGAAAACCCTACAATCAAAAACCTAGCTCCGACCATCGGCTCATCGG  1725
                                                               ClaI
                                                               |
1726  TGCCGAAGGTGTAACCTTTCNCTCCCATCATAGTTTCTCGTAATGAAAGCTAATTGGGCAATCGATTT  1794
                                     1789
1795  TTTAATGTTTAAACCATGCCAAGCCATTTCTTATAGGACAATTGTCAATAATAGCATCTTTTGAGTTTT  1863
1864  GTCTCAAAAGTGACACTAGAGAAGAAAATGACATTCATTAAAAAGTAAAAATATCCCTAA  1932
1933  TACCTTTGGTTTAAATTAAAATAAGTAAACAAATAAAAACAAATAAAATAAAAAATAAAAAATGA  2001
2002  AAAAAAGAAATTTTTTTTATAGTTTCAGATTATATGTTTCAGATTCGAAATTTTTTAAA  2060
```

FIGURE 5
Page 3 of 3

```
        XhoI
     1  CTCGAGAGCTGAAGGATTTTTGTTAGAGATTCAACGACAGATGGACCCTTCCTCCACTAGGCAACTGC     69
        2

70  AAGAACCTAACAATGCAAATATCACTCCTCCTCAGCCTTCAAGGAGCGTTAATAGGACTGGAACAAGCG    138
                                                     BglII
                                                     |
   139  GTCAAGTGAGTAAATTTCCTTCCAAGATATAGATCTCTATGGTTCGGTTCATGAAGTTTGTGGTTTAATT   207
                                                 169

208  GTGTAGCAACAGGATAGTGCAAGTGAGAATAGAGTTCGACCCTCATCTACCTACCCCCGGAACCTCTGAAT   276

277  GTATCCCCATTGAAGAAGAGAGGCAAATCCTGCACCCAGAAGGATAAAGAAATTTTGGACGCCTGAA      345

346  GAAGTGGCAGTTCTGAGGAAGGAGTAAAAGAGTATGTCTACTACTACTCTATAATCAAGTTTCAA        414

415  GAAGCTGAGCTTGGCCTCTCACTTTATATGTTTGATGTGTTGTGCAGGTATGGTAAATCATGGAAAGAG    483

484  ATAAAGAATGCAAACCCTGAAGTTGTAACTGGTACTAAAAGGTTTGTAACTTTTGGTAGGTGGAT        552

553  CTCATCTGAATTATCTTATATGCGAATTGCTTCCGGTAGCCGGTAACAAGTTTTATATTGCTATGAAGTTTTTTG  621

622  TTGAAGGATAAATGGAGAAGAACTTGCTTCCGGTAGCCGGTAACAAGTTTTATATTGCTATGAAGTTTTTTG    690

691  CCTGCGTGACGTATCAGCAGCTGTGGAGAAGATGGTATTAGAAAGGTCTTTCACATTTTGTTGTG         759

760  ACAAATATTAATTCGGCCGGTATGGTTTGGTTAAGACTTGTTGAGAGACGTGGGGTTTTTGATGTA        828
```

829  TAATTAGTCTCTGTGTTTAGAACGAAACAAGACTTGTTGCGTATGCTTTTTTTAACTTGAGGGGGTTTGTT  897

898  GTTGTTAGTTAGGAACTTGACTTTGTCTCTTTCTCTCAAGATCTGATTGGTAAGGTCTCGGGTGGTAGTA  966
                                         BglII
                                          937

967  CTGTTTGGTTTAATTTGTTTTTGACTATTGAGTCACTGTGGCCCATTGACTTTAAATTAGGCTGGTATAT  1035

1036 TTTTTGGTTTAAAACCGGTCTGAGATAGTCAATTTCGATTCAGTCAATTTTAAATTCTTCAAGGTAAT  1104

1105 GGGCTGAATACTTGTATAGTTTTAAGACTTAACAGGCCTAAAAGGCCCATGTTATCATAAAACGTCAT  1173
                            HindIII
                             1190

1174 TGTTTTAGAGTGCACCAAGCTTATAAAATGTAGCCAGGCCTTAAAAGACTTAACAGGCCTTAAAAGACTT  1242

1243 AACATTCCTTAAAAGGCCCATGTTATCATAAAAACGTCATCGTTTTGAGTGCACCAAGCTAAATGTAGCC  1311

1312 AGGCCTTAAAAGACTTAACAGGCCTAAAAGGCCCATGTTATCATAAAACGCCGTCGTTTTGAGTGCAC  1380
       HindIII
        1383

1381 CAAGCTTATAAAATGTAGCCAGCTACCTCGGGACATCAGCTCTTTGTACACTCCGCCATCTCTCTCT  1449
       XhoI   BglII                                          SalI
       1451   1458                                            1484

1450 CTCGAGCAGATCTCTCTCGGGAATATCGACAATGTCGACCACTTTCTGCTCTTCCGTCTCCATGCAAGC  1518

FIGURE 6
Page 2 of 5

```
1519 CACTTCTTCTGGTAATCTCCATCTCCTTCTTGTGTTCCCAGATCGCTCTGATCATACTTTCTTTTAGATCA 1587
1588 TTTGCCTCTGATCTGTGTGCTTGTTGTTAACTCTCCACGCATGTTTGATTATGTTGAGAATTAGAA 1656
1657 AAAAAATGTTAGCTTTACGAATCTTTAGTGATCATTTCAATTGGATTTGCAATCTTGTGTGACATTTGA 1725
1726 GGCTTGTGTAGATTTCGATCTGTATTCATTTGAATCACAGCTATAATAGTCATTTGAGTAGTAGTGTT 1794
1795 TTTAAATGAACATGTTTGTTGTATTGATGGAACAAACAGGCAGCAACAACGAGGATTAGTTTCCAGAA 1863
1864 GCCAGCTTTGGTTTCAACGACTAATCTCCCTTCAACCTCCCGCCGTTCAATCCCCACTCGTTTCTCAAT 1932
1933 CTCCTGCGCGGTATGTTCTCATTCTCAGCATTTATTTCGAGCTTGCTTGTCATGGTACTCTCTAATT 2001
2002 GTCTATTTGGTTTATTAGGCCAAACCAGAGACGGTTGAGAAAGTGTCTAAGATAGTTAAGAAGCAGCTA 2070
2071 TCACTCAAAGACGACCAAAAGGTCGTTGCGGAGACCAAGTTTGCTGATCTTGGAGCAGATTCTCCGAC 2139
2140 ACTGTAAGTCATCAATCATTCTCTTATGTGAATAAAGAGAACTTGAAGAGTTTGTTTTAACATATTAA 2208
                                                                    EcoRV
                                                                     2264
2209 CTGAGTGTTTTGCATGCAGGTTGAGATAGTGATGGGTTTAGAGGAAGAGTTTGATATCGAAATGGCTGA 2277
                                                        SstI
                                                         2335
2278 AGAGAAAGCTCAGAAGATTGCTACTGTGGAGGAAGCTGCTGAACTCATTGAAGAGCTCGTTCAACTTAA 2346
2347 GAAGTAATTTTAGTATTAAGAGACAGCCAAGGCTTTGTTGGGTTTGTTGTTTTCATAATCTTCCTGTCAT 2415
```

FIGURE 6
Page 3 of 5

```
2416  TTTCTTTTTCTTTAATGTGTCAAGCCGACTCTGTGTTGGTTTAAAGTAGTATCTGTTTGCCATGGATCTCTC  2484
                   SalI                            HindIII
                   ---                             -------
2485  TCTATTTGTCGACTGAAAACTTTTGGTTTACACATGAAAGCTTGTTCTTGTTCTTTCTTAAATCGAAAT  2553
                   2493                         2523
2554  GCCAAATGCGAGATTAGGGAATCTTGTATTAACACATACATAAGTCAAAGAGTAGGCCCTAAGATGACA  2622
2623  ATTTATAAACAATCCTATTCACATTGTATATACAGGTTATGATTATTCCCAATCAGCGTCAAAGAATCC  2691
2692  AGCATCTTTCATCTCTGAATAGTAGACATTCTCCAAGTTCACATCTTCCTCCTGCACCAAAACCAGTA  2760
2761  CTAAATCATGAACATTGCAATAATCACATGCCTAGGCGAGAGTTTTGGTGATGTGGTGTAGTGATAGT  2829
2830  GATACTGATGGTGCTAGAGCGGTTAAGAAGGATTAACCTGGAAGAAGTCTGCAAGGAAGTAACATAGA  2898
2899  GAAGAGGAAGATAGGAGTGGTAACAAACAAGAGAAGTCTGACTAGATGATATTTATATAGGATAAGTGTTTCAAATGTT  2967
2968  ATTTCCTTACATAAAGAAAACAAGAGAAGTCTGACTAGATGATATTTATATAGGATAAGTGTTTTACCAT  3036
3037  AAGCCAAAGTGAGCGCCGTTTGCAAGAGCTAACCAGACAGTAACACAGTACACGTTTGGCATATATCTCATCAACAT  3105
3106  GATCTGAAAAGTAACATATCACAGTGTTACCTTGAGAAGCAAATCAAGACCTATA  3174
3175  ACAAGCCCAGAGATGAGGAAAGTCCGTGTCAACGCTTCACCGCCATTCGCGTAGTTCCTTGGAAGACA  3243
3244  AAGGCCACCAACCAAACTTACTTCCAGAAAACAACACTCCAAATGTTGTCAACAAGTCAATAGATTCCA  3312
3313  AACTACTTCGTTACAGGGTTGTATAGATAATATAATAGAATAGTGGGAAGATAGTATAAATAAATAAA  3381
```

FIGURE 6
Page 4 of 5

```
3382  TAAAAGATCCTATCGGTAAATAGTTTATATAATATCGGGGCGTATATAAAGTATAAAGAAACTCTTCTC  3450
3451  CAATCCGACCGTTGAAAATCACTCTCAATCTCTGGCGTAACGACCGGATCGTTCGCGCGTAATTTTCGC  3519
3520  TGCTATAAATAGAAACTTTCCTCTTCTCTGTTTCTCGATCAAAATTTTTTTTGGAAAAATTAAGTTTGAA  3588
3589  TCTATCGTAGATGCTGTGTGACAAAAAAAAATTGTTTTATCGAAGATGAGAAACATGAGGCCTGTTCATGC  3657
                                                                    BamHI
                                                                    |
                                                                    3674
3658  AAGGAACCAGACCACGGATCCATCTTCGCCGATGATGACGTCTCCTCTGATGAATCGTCACGCACGGAC  3726
             BamHI
             |
             3729
3727  AGGATCCAACGCTGGACCAGCATCTAACGCCAAGAAAGCCACAGACGAAAGCAGCTCAGAGACTCGC  3795
3796  GGCTGTGATGTCGAACCAAACAGGCGACGATGAAGACAGTGATGATGACCTTTCCTTTGACTACAACGC  3864
                                                         BglII
                                                         |
                                                         3894
3865  TGTCGGAAGCATTGGTCTCGCTGCCGGAAGATCT  3898
```

FIGURE 6
Page 5 of 5

1/14

```
                                                                                    EcoRV
346  AAAACATTTTTTGCATATACACTTTGAAAGTTCCTCACTAACTGTGTAATCTTTTGGTAGATATCACTA  414
                                                                    408

HincII
                     HhaI
                     HaeIII
                     DdeI                              HaeIII        AluI
                     BstEII
                     BalI
415  CAATGTCGGAGAGACAAGGCTGCGCCAGCATATACAAAAGGGAAATGAAGATGGCCTTTTGATTAGCTG  483
                     439                                       469        481
                     438
                     439
                     439
                     440
                     438

HinfI
484  TGTAGCATCAGCAGCTAATCTCTGGGCTCTCATCATGATGCTGGAACTGGATTCACTTCTCAAGTTTA  552
           AluI                                       535
              498

MapI                                           HinfI
        HpaII
553  TGAGTTGTCACCGGTCTTCCTACACAAGTAATAATCAGTTGAAGCAATTAAGAATCAATTTGATTTGT  621

Figure 7
                                     2/14
```

```
                                                              606
              564
              564                                                                                                 690
                    AGTAAACTAAGAAGAACTTACCTTATGTTTCCCCGCAGGACTGGATTATGGAACAATGGGAAAAGAAC
        622
                    DdeI
                         629

AluI  AluI          SacI
                                                  AluI                                                            759
        691         TACTATATAAGCTCCATAGCTGGTTCAGATAACGGGAGCTCTTTAGTGTTATGTCAAAAGGTTAGTGT
                                     702   710          729
                                                        731

828
        760         TTAGTGAATAATAAACTTATACCACACAAAGTCTTCATTGACTTATTTATATACTTGTTGTGAATTGCTAG

DdeI            HinfI                                                      897
        829         GAACTACTTATTCTCAGCAGTCATACAAAGTGAGTGACTCATTTCCGTTCAAGTGGATAAATAAGAAAT
                                          842                865

XmnI                                                                       TaqI

```
3451 ATATGACATCACCTAGAGAAAGCCGATAATAGTAAACTCTGTTCTTGGTTTTTGGTTTAATCAAACCGA 3519

MapI
                                                    HpaII
         MspI  DdeI                          NdeI   HinfI
         HpaII AluI                            |      |
          |  |   |                             |      |
3520 ACCGGTAGCTGAGTGTCAAGTCAGCAAACATCGCAAACCATATGTCAATTCGTTAGATTCCCGGTTTAA 3588
         3522 3528                             3560      3576
         3522 3529                                             3581
                                                               3581
          MapI
          HpaII
           |
3589 GTTGTAAACCGGTATTTCATTTGGTGAAAACCCTAGAAGCCAGCCACCCTTTTTAATCTAATTTTTGCA 3657
              3598
              3598

HinfI
                                                              HincII
                                                        DdeI  BstNI
                                                         |     ||
3658 AACGAGAAGTCACCACCACCTCTCCACTAAACCCTGAACCTTACTGAGAGAAGCAGAGCGCACTCAAAGAA 3726
                                            3702             3718
                                                          3715
                                                          3714

3727 CAAATAAAACCCGAAGATGAGACCACCACGTGGCGGGAGCTTCAGGGGACGGGGAGGAAGAGATGG 3795
```

Figure 7

```
                 AvaII
                 AluI                                                                        AvaII
                  |                                                                           |
 3796 CGGCGGACGCTTTGGTGGCGGGCGGACGTTTTGGTGGCGGGCGGTGGA 3864
               3801                                      3863
           3804

EcoRV     AvaII                              DdeI
             |         |                                 |
 3865 CGCTTTGGTGGTGGATATCGTGACGAAGGACCTCCCAGTGAAGTCATTGGTTCGTTTACTCTTTTCTTAG 3933
                  3880       3892                              3930

TaqI                                      HindIII
      HinfI                                     AluI                      DdeI
        |                                        |                         |
 3934 TCGAATCTTATTCTTGCTCCTCGCTCGTTGTTTTACCGATAAAGCTTAAGACTTTATTGATAAAGTTCTCA 4002
       3935                                     3976                      4000
      3937                                     3974

AluI            XmnI                                     HinfI    DdeI
        |               |                                         |       |
 4003 GCTTTGAATGTGAATGAACTGTTCCTGCTTATTAGTGTTCCTTTGTTTTGAGTTGAATCACTGTCTTA 4071
                        4023                                    4059  4069

HinfI
        |
 4072 GCACTTTTGTTAGATTCATCTTTGTGTTTAAGTTAAAAGGTAGAAACTTTGTGACTTGTCTCCGTTATG 4140

PLANT STEAROYL-ACP DESATURASES GENES

This is a continuation of appliction Ser. No. 07/494,106, filed Mar. 16, 1990, now abandoned.

TECHNICAL FIELD

The present invention is directed to a protein relevant to fatty acid synthesis in plants, methods to purify the protein to homogeneity, amino acid and nucleic acid sequences related thereto, and methods of use for such compositions.

INTRODUCTION

BACKGROUND

Improved means to manipulate fatty acid compositions, from biosynthetic or natural plant sources, are needed. For example, edible oil sources containing the minimum possible amounts of saturated fatty acids are desired for dietary reasons and alternatives to current sources of highly saturated oil products, such as tropical oils, are also needed.

Higher plants appear to synthesize fatty acids via a common metabolic pathway in plant plastid organelles (i.e., chloroplasts, proplastids, or other related organelles) as part of the Fatty Acid Synthase (FAS) complex. Fatty acids are used in plant membranes and in neutral lipids that are formed for energy storage in developing seed tissues, and the like.

Unsaturated fatty acids originate from the desaturation of stearoyl-acyl carrier protein (hereinafter "acyl carrier protein" may also be referred to as "ACP") to form oleoyl-ACP, a monounsaturated fatty acid, in a reaction catalyzed by a soluble plastid delta-9-desaturase, also known as "stearoyl-ACP desaturase". Thus, in the plant FAS pathway, stearoyl-ACP desaturase catalyzes the production of the monounsaturate oleoyl-ACP (C18:1-ACP) from saturated stearoyl-ACP (C18-ACP). The desaturase enzyme functions to add a first double bond in the eighteen member long stearoyl-ACP carbon chain in accordance with the following reaction (I):

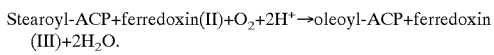
Stearoyl-ACP+ferredoxin(II)+O$_2$+2H$^+$→oleoyl-ACP+ferredoxin (III)+2H$_2$O.

Unreacted stearoyl-ACP and oleoyl-ACP may be further metabolized to produce stearic and oleolic fatty acid residues. In plant species naturally low in saturated fat content (e.g., safflower, rapeseed), it is noted that greater than 90% of all stearoyl-ACP synthesized is converted on to the oleoyl thioester.

Stearoyl-ACP desaturase has been studied in partially purified preparations from numerous plant species. Reports indicate that the protein is a dimer, perhaps a homodimer, displaying a molecular weight of 68 kD (±8 kD) by gel-filtration and a molecular weight of 36 kD by SDS-polyacrylamide gel electrophoresis.

Relevant Literature

A 200-fold purification of safflower stearoyl-ACP desaturase was reported by McKeon & Stumpf in 1982, following the first publication of their protocol in 1981. McKeon, T. & Stumpf, P. *J.Biol.Chem.* (1982) 257:12141–12147; McKeon, T. & Stumpf, P. *Methods in Enzymol.* (1981) 71:275–281.

BRIEF DESCRIPTION OF THE DRAWINGS

FIG. 1 shows a partial amino acid sequence fragments of safflower stearoyl-ACP desaturase. Each fragment represents a synthsesis of sequence information from peptides originating from different digests which have been matched and aligned. In positions where there are two amino acids indicated, the top one corresponds to that found in the translation of the cDNA; the lower one was detected either as a second signal at the same position of one of the sequenced peptides, or as a single unambiguous signal found in one or more of the overlapping peptides comprising the fragment. Residues in F9 shown in lower case letters represent positions where the called sequence does not agree with that predicted from the cDNA, but where the amino acid assignment is tentative because of the presence of a contaminating peptide. The standard one letter code for amino acid residues has been used. X represents a position where no signal was detectable, and which could be a modified residue. F1 corresponds to the N-terminal sequence of the mature protein. The underlined region in F2 is the sequence used in designing PCR primers for probe synthesis.

FIG. 2 shows the complete cDNA sequence and the corresponding translational peptide sequence derived from the cDNA is shown of safflower stearoyl-ACP desaturase. The complete cDNA sequence includes both the plastid transit peptide encoding sequence (underlined) and the sequence encoding the mature protein.

FIG. 3 shows the design of forward and reverse primers used in polymerase chain reaction (PCR) from the sequence of safflower stearoyl-ACP desaturase peptide "Fragment F2".

FIG. 5 shows approximately 2 kb of genomic sequence of Bce4.

FIG. 6 shows approximately 4 kb of genomic sequence of Bcg 4—4 ACP sequence.

SUMMARY OF THE INVENTION

Figure 4:
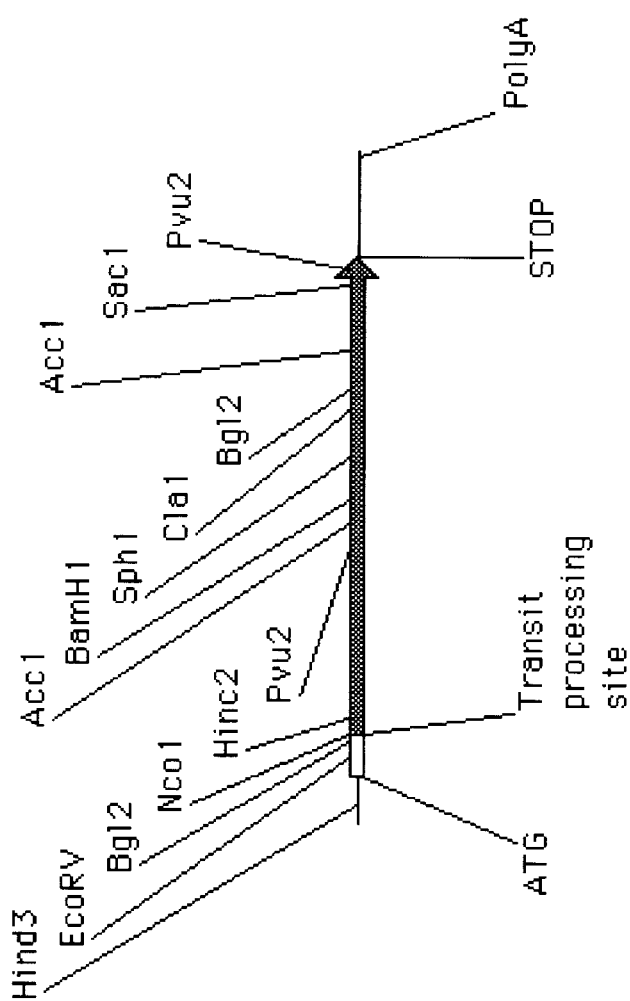
FIG. 4 is representation of the safflower stearoyl-ACP cDNA showing selected restriction enzyme sites.

A first aspect of this invention relates to safflower stearoyl-ACP desaturase substantially free of seed storage protein. Amino acid sequence of the safflower stearoyl-ACP desaturase is exemplified in FIG. 1.

This invention also relates to methods for obtaining plant stearoyl-ACP desaturase. By contacting an antibody specific to safflower stearoyl-ACP desaturase with a plant stearoyl-ACP desaturase under conditions conducive to the formation of an antigen:antibody immunocomplex and the recovery of plant stearoyl-ACP desaturase which reacts thereto.

In yet a different embodiment of this invention, plant stearoyl-ACP desaturase cDNA of at least 10 nucleotides or preferably at least 20 nucleotides and more preferably still at least 50 nucleotides, homologously related to safflower stearoyl-ACP desaturase is also provided. The cDNA encoding precursor stearoyl-ACP desaturase or, alternatively, biologically active, mature stearoyl-ACP desaturase is provided herein. cDNA sequence of safflower stearoyl-ACP desaturase and sequences homologously related thereto, having at least 60, more preferably 70% homologous relationship with the safflower stearoyl-ACP desaturase, are also provided.

In yet a different embodiment, this invention relates to a plant stearoyl-ACP desaturase obtained by the steps of contacting a nucleic acid sequence probe comprising nucleotides of safflower stearoyl-ACP desaturase sequence, under stringent hybridization conditions, and recovery of plant stearoyl-ACP desaturase having hybridized with the probe.

In a further aspect of this invention DNA constructs comprising a first DNA sequence encoding a plant stearoyl-ACP desaturase and a second DNA sequence which is not naturally found joined to said plant stearoyl-ACP desaturase are provided. Constructs of this invention may contain, in the 5' to 3' direction of transcription, a transcription initiation control region capable of promoting transcription in a host cell and a DNA sequence encoding plant stearoyl-ACP desaturase. Transcription initiation control regions capable of expression in prokatyotic or eukaryotic host cells are provided. Most preferred are transcription initiation control regions capable of expression in plant cells, and more preferred are transcription and translation initiation regions preferentially expressed in plant embryo tissue during the period of lipid accumulation. The plant stearoyl-ACP desaturase of this invention may be found in either the sense and anti-sense orientation to the transcription initiation control region.

In yet a different embodiment, DNA constructs having in the 5' to 3' direction of transcription, a transcription/translation initiation control region comprising sequence immediately 5' to a structural gene preferentially expressed in plant embryo tissue during lipid accumulation, a DNA sequence encoding an enzyme having plant stearoyl-ACP desaturase activity and sequence 3' to the structural gene. The construct will preferably contain plant stearoyl-ACP desaturase obtained from safflower stearoyl-ACP desaturase. Transcription/translation initiation control regions are preferentially obtained from structural genes preferentially expressed in embryo tissue such as napin, seed-ACP or Bce-4.

In yet a different embodiment, this invention is directed to a method of producing plant stearoyl-ACP desaturase in a host cell comprising the steps of growing a host cell comprising an expression cassette, the expression cassette would contain in the direction of transcription, a) a transcription and translation initiation region functional in said host cell, b) the DNA sequence encoding a plant stearoyl-ACP desaturase in reading frame with said initiation region, and c) and a transcript termination region functional in said host cell, under conditions which will promote the expression of the plant desaturase.

DETAILED DESCRIPTION OF THE INVENTION

A plant stearoyl-ACP desaturase (hereinafter sometimes referred to as "desaturase") of this invention includes any sequence of amino acids, such as a protein, polypeptide, or peptide fragment, whether obtained from plant or synthetic sources, which demonstrates the ability to catalyze the production of a C18:1 from a C18:0 fatty acid-ACP moiety. For example, plant desaturase includes modified amino acid sequences, such as sequences which have been mutated, truncated, increased and the like, as well as such sequences which are partially or wholly artificially synthesized, so long as the synthetic sequence retains the characteristic desaturase activity. A plant stearoyl-ACP desaturase also may be considered as any amino acid sequence which is obtainable from safflower stearoyl-ACP desaturase through the use of nucleic acid probes, antibody preparations, or sequence comparisons, for example. Approximately 90% of the total amino acid sequence of the safflower stearoyl-ACP desaturase is provided in FIG. 1.

In order to obtain the nucleic acid sequences encoding plant stearoyl-ACP desaturase, especially safflower stearoyl-ACP desaturase, safflower desaturase free of a major safflower albumin-type contaminant was required. As demonstrated more fully in the Examples, the protocols of McKeon and Stumpf, supra, result in a preparation contaminated with a seed storage protein. Removal of the protein contaminant may be effected by application of a reverse-phase HPLC, or alternatively, by application of a reduction and alkylation step followed by electrophoreses and blotting, for example. Other purification methods may be employed as well, now that the presence of the contaminant is confirmed and various properties thereof described. Once the purified safflower stearoyl-ACP desaturase is obtained it may be used to obtain the corresponding amino acid and/or nucleic acid sequences thereto in accordance with methods familiar to those skilled in the art. Of particular interest is the DNA sequence which encodes the plant desaturase.

DNA sequence which encodes plant stearoyl-ACP desaturase may be employed as a gene of interest in a DNA construct or as probes in accordance with this invention. When found in a DNA construct for integration into a plant genome, the plant desaturase may be found in a sense orientation or anti-sense orientation. By increasing the amount of desaturase available to the plant fatty acid synthase (FAS) complex, an increased percentage of unsaturated oils may be provided; by decreasing the amount of desaturase available to the FAS, an increased percentage of saturated oils may be provided in vivo.

Sequences found in a sense orientation may be found in "expression cassettes," DNA constructs which allow for the transcription and translation of the plant stearoyl-ACP desaturase in the plant host cell. The resulting desaturase enzyme may act to decrease the amounts of saturated fatty acids found in the target tissue. Thus, of special interest is the production of oils having increased levels of oleate. Sequences found in an "anti-sense" orientation may be found in cassettes which at least provide for transcription of the DNA sequence encoding the plant desaturase. By anti-sense is meant a DNA sequence in the 5' to 3' direction of transcription which encodes a sequence complementary to the sequence of a sense plant desaturase. It is preferred that an anti-sense plant desaturase sequence be complementary to the plant desaturase found in the plant host cell. Using anti-sense technology, a decrease in the amount of desaturase available to the cell is expected, resulting in a higher percentage of saturates, of special interest is the production of oils having increased levels of stearate.

The degeneracy of the DNA code provides that some codon substitutions are permissible of DNA sequences encoding a plant stearoyl-ACP desaturase. When a DNA sequence encoding plant desaturase is to be expressed in a plant host cell, the use of "plant preferred codons" is desirable.

A DNA sequence of this invention may include genomic or cDNA sequence. A cDNA sequence may or may not contain preprocessing sequences, such as transit peptide sequences. Transit peptide sequences facilitate the delivery of the protein to a given organelle and are cleaved from the amino acid moiety upon entry into the organelle, releasing the "mature" sequence. In FIG. 2, the complete sequence of the safflower stearoyl-ACP desaturase precursor protein is provided; both the transit peptide and mature protein sequence are shown. The use of the precursor cDNA sequence is preferred in plant cell expression cassettes. Transit peptide sequences may be employed to translocate other proteins of interest to plastid organelles for a variety of uses, including the modulation of the FAS pathway. See, European Patent Application Publication No. 189,707.

As described in more detail below, the complete genomic sequence of the safflower stearoyl-ACP desaturase may be obtained by the screening of a safflower genomic library with a safflower stearoyl-ACP desaturase cDNA probe and isolating those sequences which regulate expression in seed tissue. In this manner, the transcription, translation initiation regions and/or transcript termination regions of the safflower desaturase may be obtained for use in a variety of DNA constructs, with or without the safflower desaturase structural gene.

Other nucleic sequences homologously related to DNA sequences encoding safflower stearoyl-ACP desaturase are also provided. "Homologously related" refers to those plant stearoyl-ACP sequences which are obtainable through the use of the safflower stearoyl-ACP desaturase of this invention. One skilled in the art will readily recognize that antibody preparations, nucleic acid probes (DNA and RNA) and the like may be prepared and used to screen and recover other plant sources for stearoyl-ACP desaturase.

Typically, a homologously related nucleic acid sequence will show at least about 60% homology, and more preferably at least about 70% homology, between the safflower stearoyl-ACP desaturase sequence and the given plant stearoyl-ACP of interest, excluding any deletions which may be present. Homology is found when there is an identity of base pairs and may be determined upon comparison of sequence information, nucleic acid or amino acid, or through hybridization reactions conducted under relatively stringent conditions, e.g., having a fairly low percentage of non-specific binding with safflower stearoyl-ACP desaturase probes.

Probes can be considerably shorter than the entire sequence, but should be at least about 10, preferably at least about 15, more preferably at least 20 nucleotides in length. Longer oligonucleotides are also useful, up to the full length of the gene encoding the polypeptide of interest. Both DNA and RNA probes can be used.

A genomic library prepared from the plant source of interest may be probed with conserved sequences from safflower stearoyl-ACP desaturase to identify homologously related sequences. Use of the entire safflower stearoyl-ACP desaturase cDNA may be employed if shorter probe sequences are not identified. Positive clones are then analyzed by restriction enzyme digestion and/or sequencing. In this general manner, one or more sequences may be identified providing both the coding region, as well as the transcriptional regulatory elements of the stearoyl-ACP desaturase gene from such plant source.

In use, probes are typically labeled in a detectable manner (for example with $^{32}$P-labelled or biotinylated nucleotides) and are incubated with single-stranded DNA or RNA from the plant source in which the gene is sought, although unlabeled oligonucleotides are also useful. Hybridization is detected by means of the label after single-stranded and double-stranded (hybridized) DNA or DNA/RNA have been separated, typically using nitrocellulose paper or nylon membranes. Hybridization techniques suitable for use with oligonucleotides are well known to those skilled in the art.

Thus, plant stearoyl-ACP desaturase genes may be isolated by various techniques from any convenient plant. Plant stearoyl-ACP desaturase of developing seed obtained from oilseed plants, such as safflower seed, soybean cotyledons, jojoba nuts, coconut, castor and the like are desired as well as non-traditional oil sources, such as spinach chloroplast, avocado mesocarp, and *Euglena gracillis*. Other candidates of special interest include rapeseed, cotton, corn and saf- flower. Of particular interest, is the safflower stearoyl-ACP desaturase cDNA sequence shown in FIG. 2.

Once the desired plant desaturase sequence is obtained, it may be manipulated in a variety of ways. Where the sequence involves non-coding flanking regions, the flanking regions may be subjected to resection, mutagenesis, etc. Thus, transitions, transversions, deletions, and insertions may be performed on the naturally occurring sequence. In addition, all or part of the sequence may be synthesized, where one or more codons may be modified to provide for a modified amino acid sequence, or one or more codon mutations may be introduced to provide for a convenient restriction site or other purpose involved with construction or expression. The structural gene may be further modified by employing synthetic adapters, linkers to introduce one or more convenient restriction sites, or the like.

The DNA sequence encoding a plant stearoyl-ACP desaturase of this invention may be combined with other, i.e. "heterologous," DNA sequences in a variety of ways. By heterologous DNA sequences is meant any DNA sequence which is not naturally found joined to the plant stearoyl-ACP desaturase, including combinations of DNA sequences from the same plant of the plant stearoyl-ACP desaturase which are not naturally found joined together.

In a preferred embodiment, the DNA sequence encoding a plant stearoyl-ACP desaturase is combined in a DNA construct having, in the 5' to 3' direction of transcription, a transcription initiation control region capable of promoting transcription in a host cell, and a DNA sequence encoding plant stearoyl-ACP desaturase with said initiation region.

Depending upon the host, the regulatory regions will vary, including regions from structural gene from viral, plasmid or chromosomal genes, or the like. For expression in prokaryotic or eukaryotic microorganisms, particularly unicellular hosts, a wide variety of constitutive or regulatable promoters may be employed. In these instances, the primary purposes for the preparation of the plant desaturase is the use of the enzyme for in vitro applications. Among transcriptional initiation regions which have been described are regions from bacterial and yeast hosts, such as *E. coli, B. subtilis, Sacchromyces cerevisiae*, including genes such as beta-galactosidase, T7 polymerase, tryptophan E and the like.

For the most part, the constructs will involve regulatory regions functional in plants which provide for modified production of plant desaturase and/or modification of the fatty acid composition. The open reading frame, coding for the plant desaturase or functional fragment thereof will be joined at its 5' end to a transcription initiation regulatory region. Numerous transcription initiation regions are available which provide for a wide variety of constitutive or regulatable, e.g., inducible, transcription of the structural gene. Among transcriptional initiation regions used for plants are such regions associated with the structural genes such as for nopaline, mannopine or with napin, acyl carrier protein (ACP) promoters and the like. The transcription/translation initiation regions corresponding to such structural genes are found immediately 5' upstream to the respective start codons. In some instances, such as modulation of plant desaturase via a plant stearoyl-ACP desaturase in an anti-sense orientation, a transcription initiation region or transcription/translation initiation region may be used. In embodiments wherein the expression of the desaturase protein is desired in a plant host, a transcription/translation initiation regulatory region, also termed "promoter" herein, is needed. Additionally, modified promoters, i.e., having transcription initiation regions derived from one gene source and translation initiation regions derived from a different gene source or enhanced promoters, such as double 35S CaMV promoters, may be employed for some applications.

Of particular interest are those 5' upstream non-coding regions which are obtained from genes regulated during seed maturation, particularly those preferentially expressed in plant embryo tissue, such as ACP-and napin-derived transcription initiation control regions. Such regulatory regions are active during lipid accumulation and therefore offer potential for greater control and/or effectiveness to modify the production of plant desaturase and/or modification of the fatty acid composition. Such "seed-specific promoters" may be obtained and used in accordance with the teachings of U.S. Ser. No. 147,781, filed Jan. 25, 1988, which is hereby incorporated by reference. Transcription initiation regions which are preferentially expressed in seed tissue, i.e., which are undetectable in other plant parts, are considered desirable for fatty acid modifications in order to minimize any disruptive or adverse effects of the gene product. For this purpose, the transcript initiation region of acyl carrier protein isolated from *B. campestris* seed and designated as "Bcg 4-4" and an unidentified gene isolated from *B. campestris* seed and designated as "Bce-4" are also of substantial interest.

The Bce-4 regulatory region is described in detail in co-pending U.S. Ser. No. (unassigned), filed contemporaneously hereto, which application entitled "Novel Promoter Preferentially Expressed in Seed" is hereby incorporated by reference. In addition, a deposit of the Bce4 gene, pCGN1857, was made at the American Type Culture Collection on Mar. 9, 1990, and assigned accession no. ATCC 68251. Briefly, Bce4 is found in immature embyro tissue at least as early as 11 days after anthesis (flowering), peaking about 6 to 8 days later or 17–19 days post-anthesis, and becoming undetectable by 35 days post-anthesis. The timing of expression of the Bce4 gene closely follows that of lipid accumulation in seed tissue. Bce4 is primarily detected in seed embryo tissue and to a lesser extent found in the seed coat. Bce4 has not been detected in other plant tissues tested, root, stem and leaves.

Approximately 2 kb genomic sequence of Bce4 is provided in FIG. 5, including about 5' to the structural gene, about 0.8 kb of the Bce4 structural gene sequence, and about 1 kb of the non-coding regulatory 3' sequence. Bce4 transcript initiation regions will contain at least 1 kb and more preferably about 5 to about 7.5 kb of sequence immediately 5' to the Bce4 structural gene.

The ACP "Bcg 4-4" regulatory region is described in detail in co-pending U.S. Ser. No. 147,781. The Bcg 4-4 ACP message presents a similar expression profile to that of Bce4 and, therefore, also corresponds to lipid accumulation in the seed tissue. Bcg 4-4 is not found in the seed coat and may show some differences in expression level, as compared to Bce4, when the Bcg 4-4 5' non-coding sequence is used to regulate transcription or transcription and translation of a plant stearoyl-ACP desaturase of this invention. Genomic sequence of Bcg 4-4 is provided in FIG. 6, including about 1.5 kb 5' to the structural gene, about 1.2 kb of the Bcg 4-4 (ACP) structural gene sequence, and about 1.3 kb of the non-coding regulatory 3' sequence.

Figure 7:
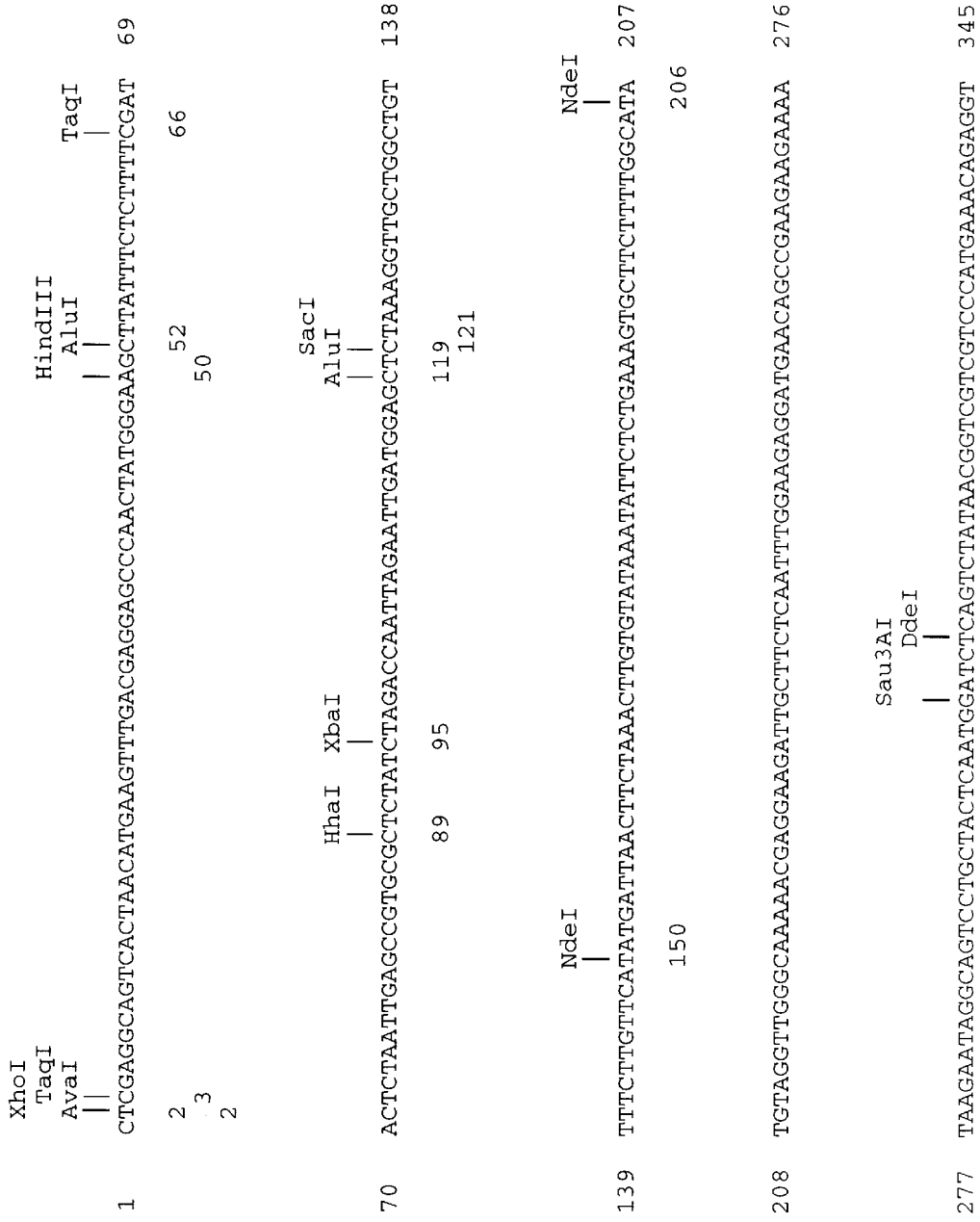
FIG. 7 shows a restriction map of cloned λCGN 1–2 showing the entire napin coding region sequence as well as extensive 5' upstream and 3' downstream sequences.
Figure 7:
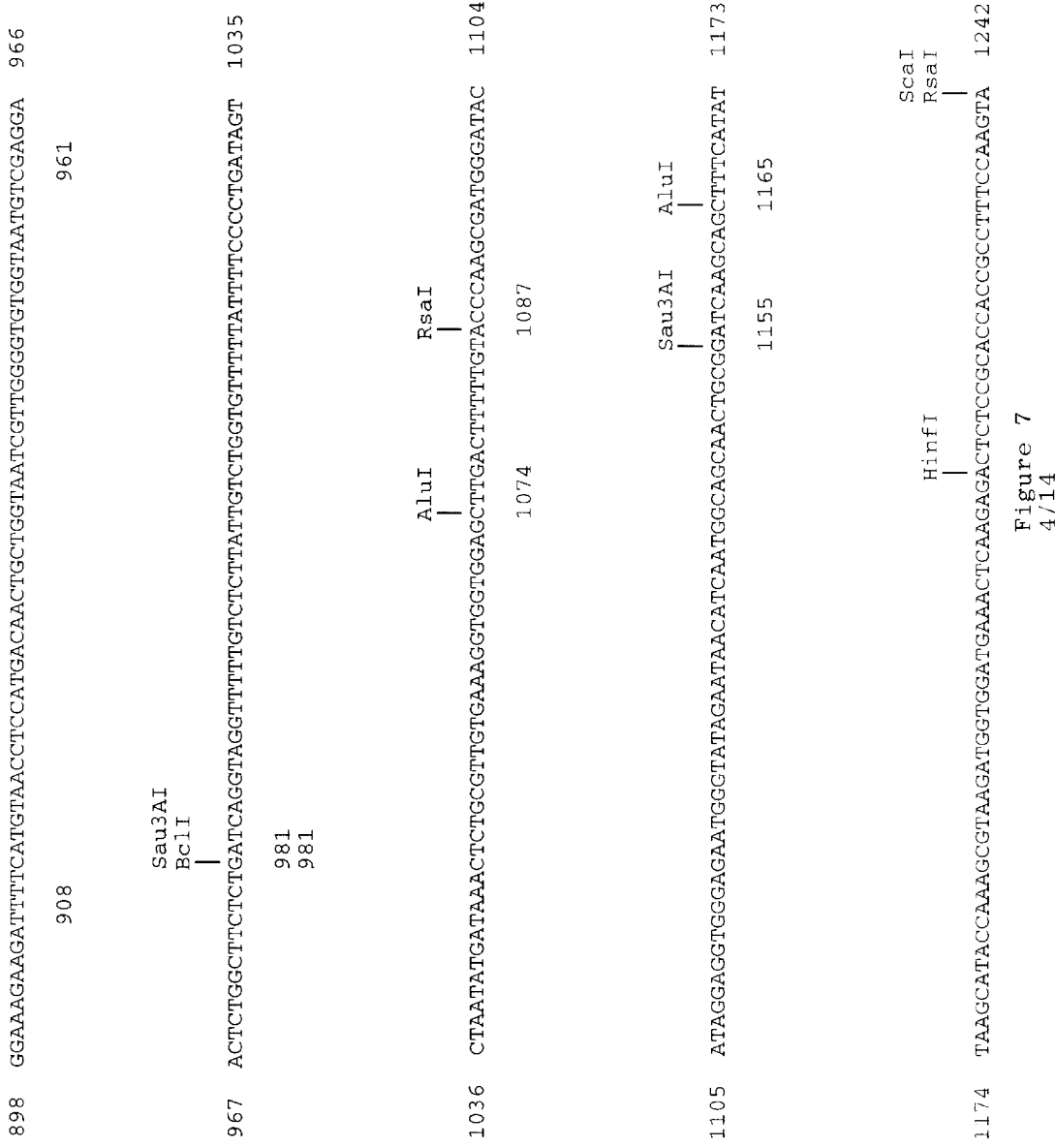
Figure 7:
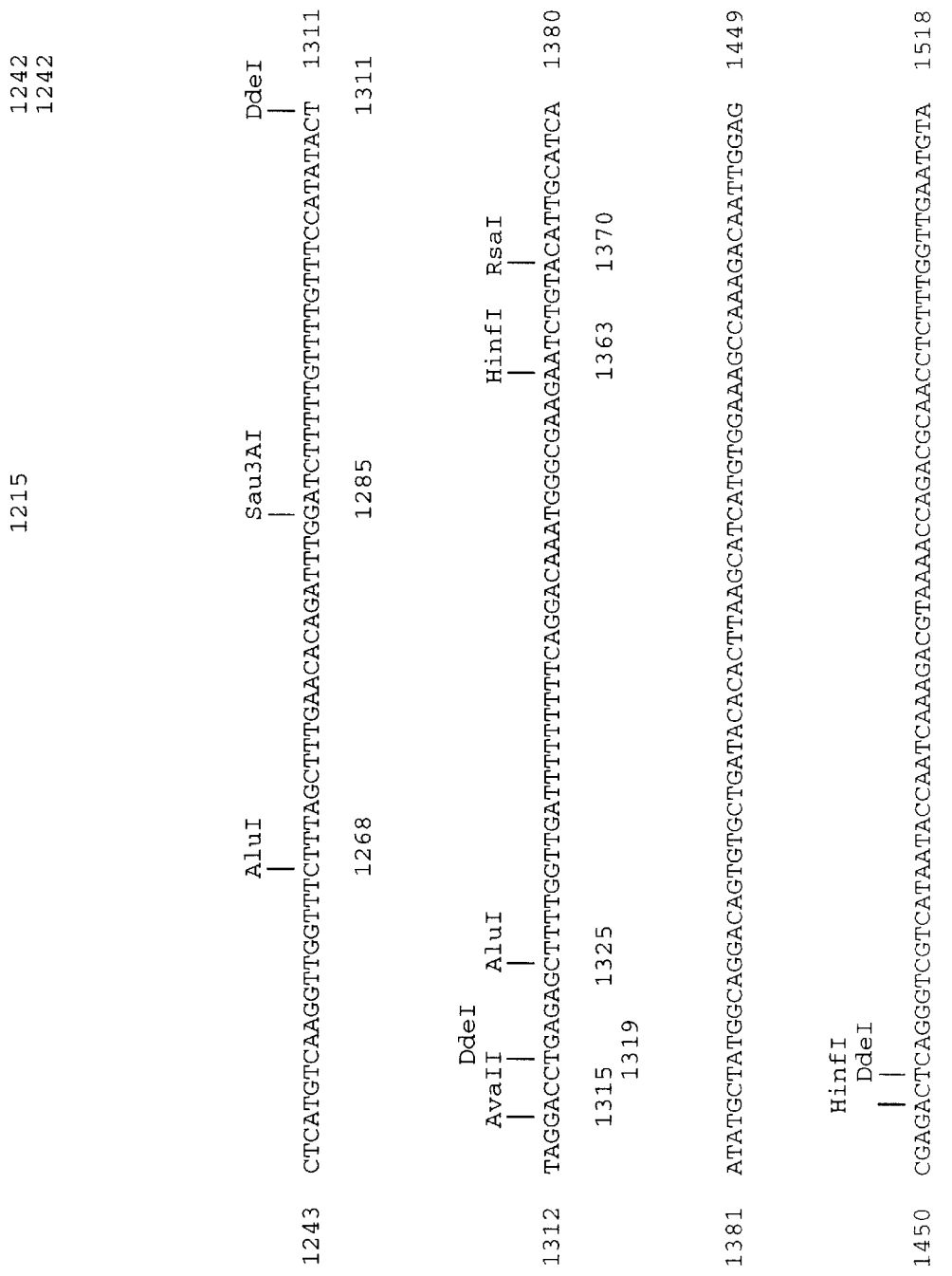
Figure 7:
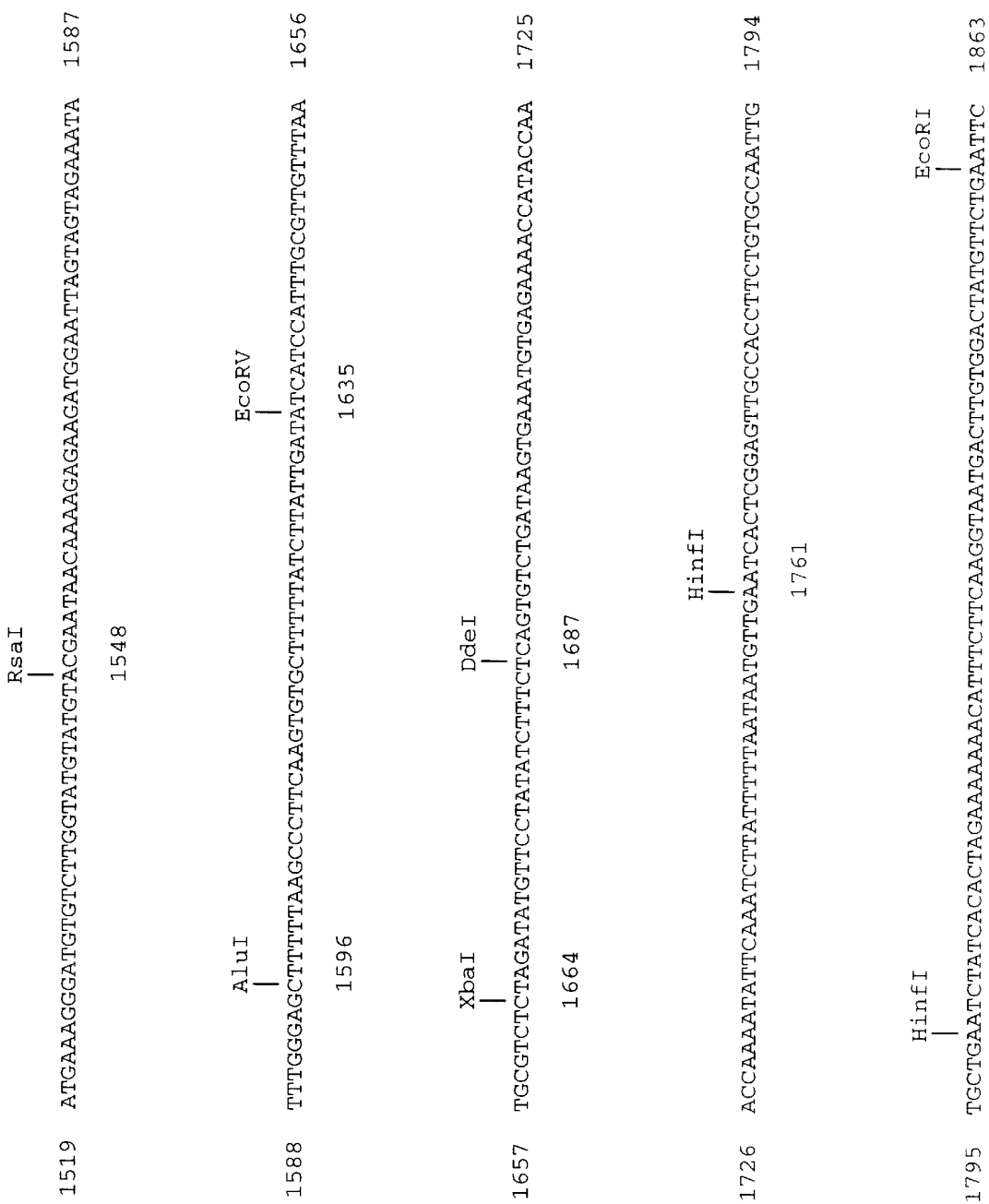
Figure 7:
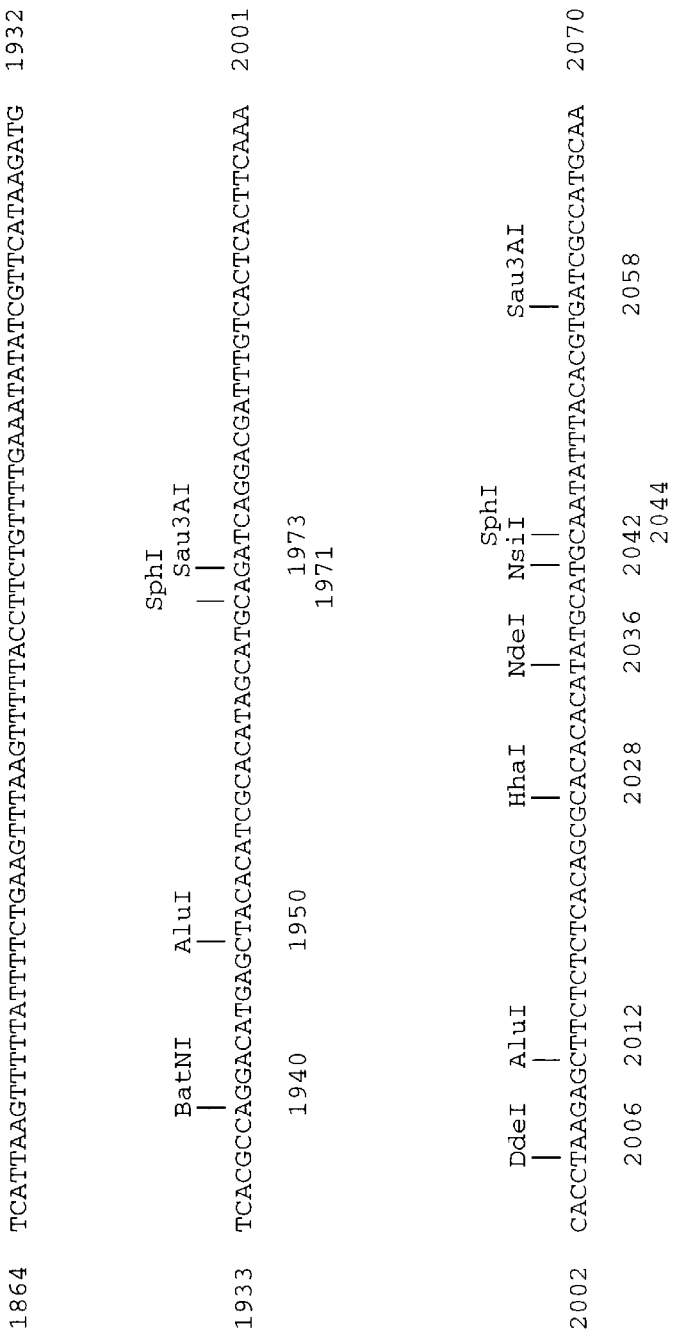
Figure 7:
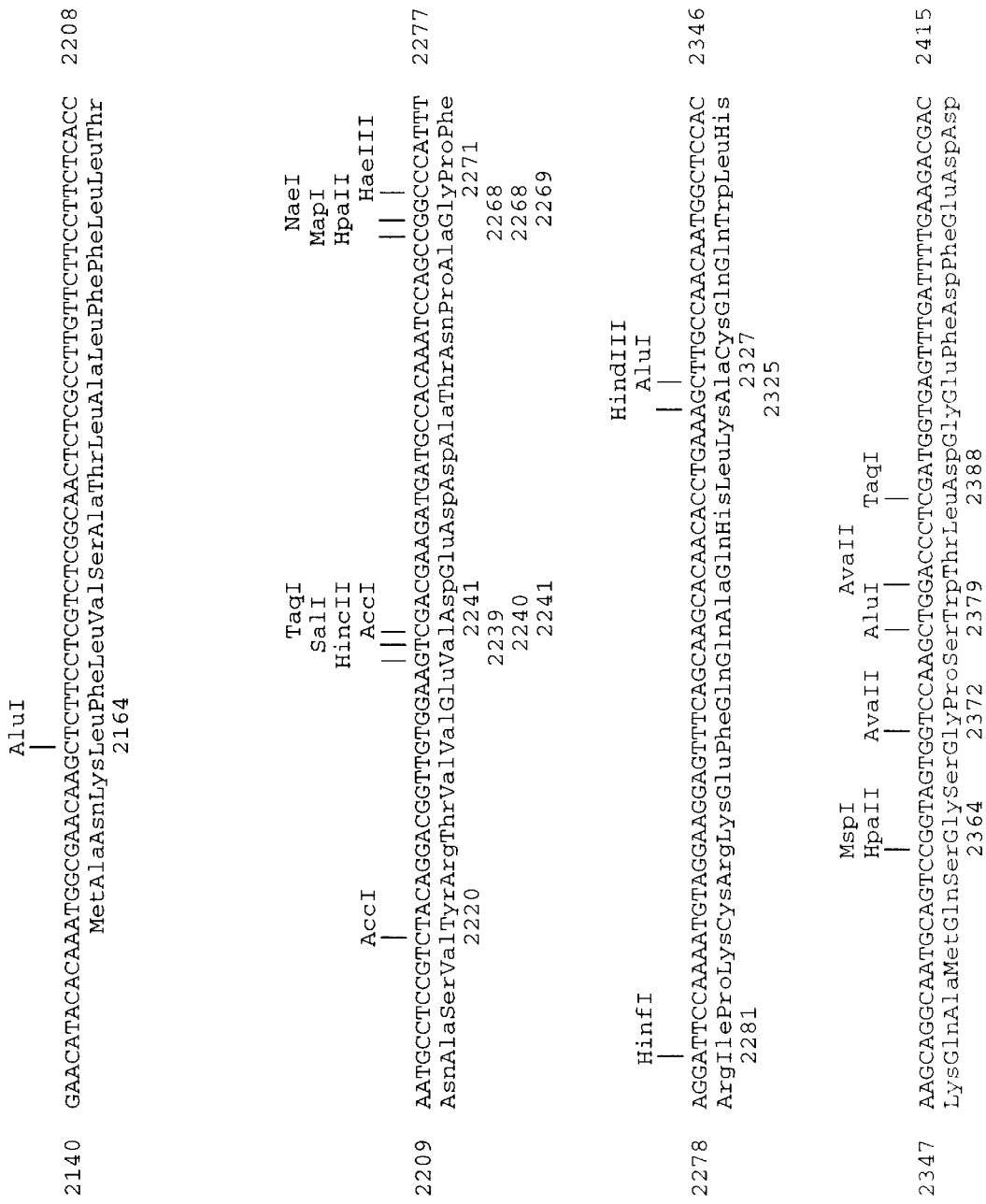
Figure 7:
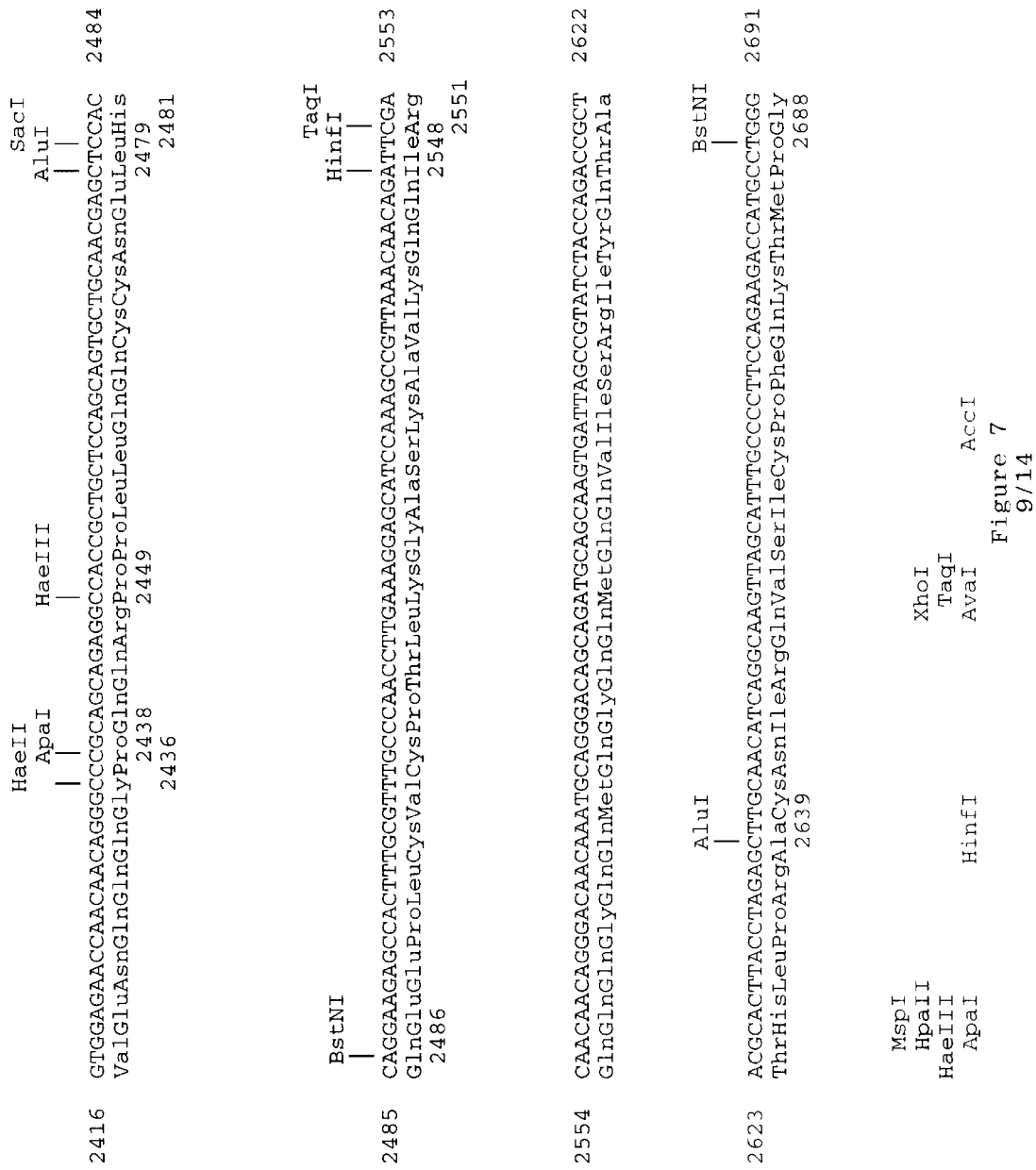
Figure 7:
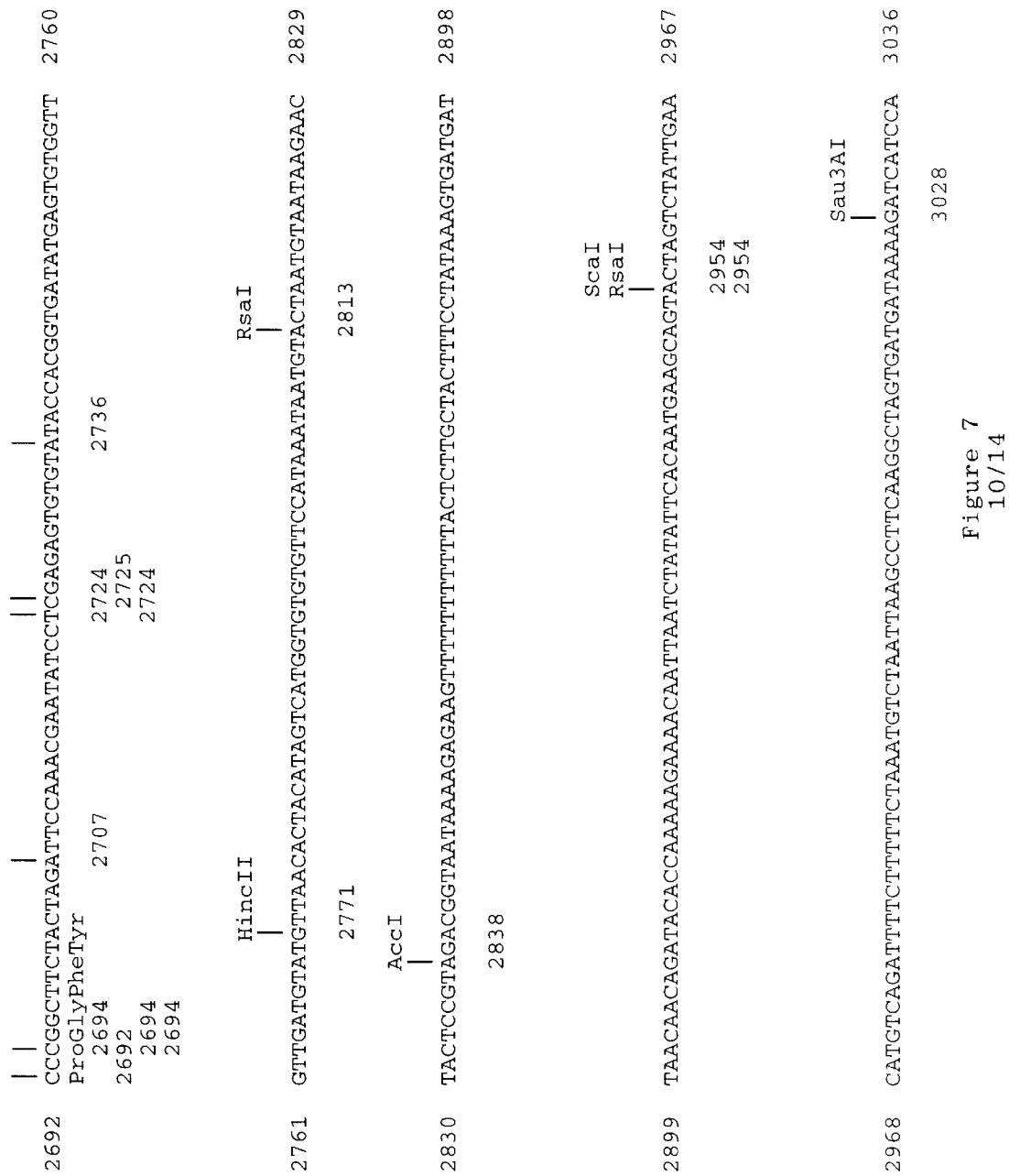
Figure 7:
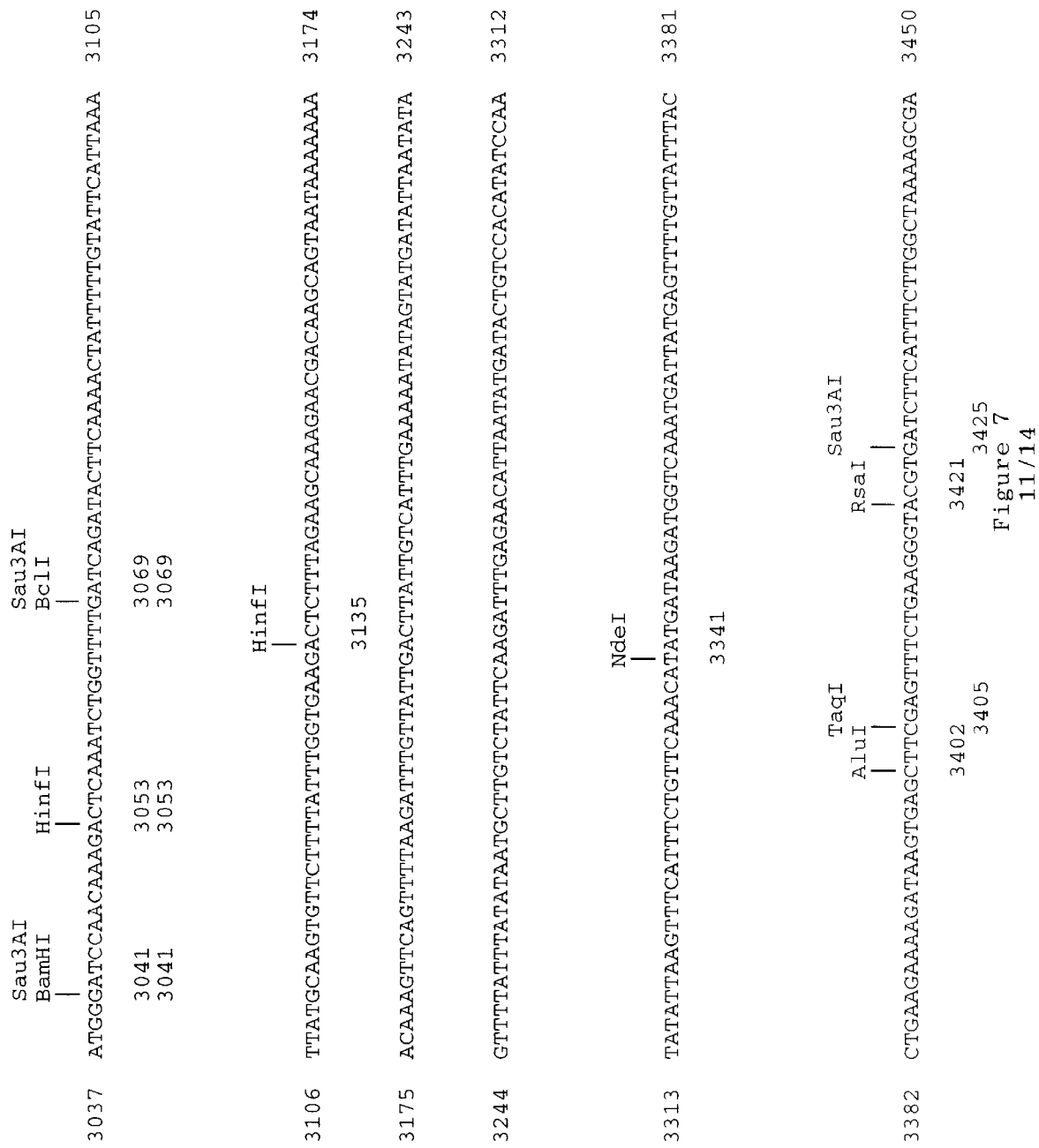
Figure 7:
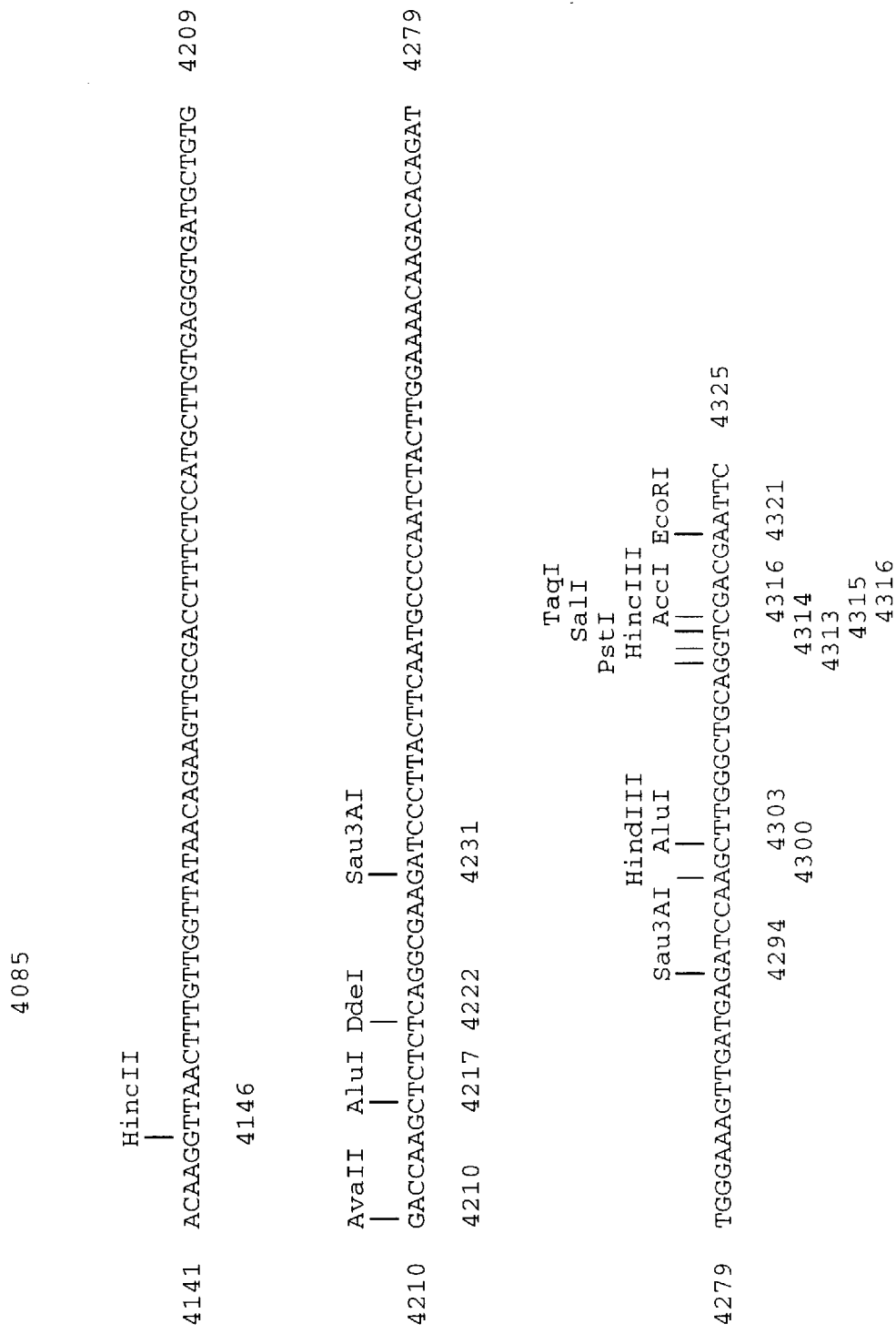

The napin "1-2" regulatory sequence is described in detail in co-pending Ser. No. 147,781. The napin 1-2 message is found in early seed development and thus, also offers regulatory regions which can offer preferential transcriptional regulation of a desired DNA sequence of interest such as the plant desaturase DNA sequence of this invention during lipid accumulation. Napins are one of the two classes of storage proteins synthesized in developing Brassica embryos (Bhatty, et al., *Can J. Biochem.* (1968) 46:1191–1197) and have been used to direct tissue-specific expression when reintroduced into the Brassica genome (Radke, et al., *Theor. Apply. Genet.* (1988) 75:685–694). Genomic sequence of napin 1-2 is provided in FIG. 7, including about 1.7 kb 5' to the structural gene and about 1.3 kb of the noncoding regulatory 3' sequence Regulatory transcript termination regions may be provided in DNA constructs of this invention as well. Transcript termination regions may be provided by the DNA sequence encoding the plant desaturase or a convenient transcription termination region derived from a different gene source, especially the transcript termination region which is naturally associated with the transcript initiation region. The transcript termination region will contain at least about 1 kb, preferably about 3 kb of sequence 3' to the structural gene from which the termination region is derived.

In developing the DNA construct, the various components of the construct or fragments therefore will normally be inserted into a convenient cloning vector which is capable of replication in a bacterial host, e.g., *E. coli*. Numerous vectors exist that have been described in the literature. After each cloning, the plasmid may be isolated and subjected to further manipulation, such as restriction, insertion of new fragments, ligation, deletion, insertion, resection, etc., so as to tailor the components of the desired sequence. Once the construct has been completed, it may then be transferred to an appropriate vector for further manipulation in accordance with the manner of transformation of the host cell.

Normally, included with the DNA construct will be a structural gene having the necessary regulatory regions for expression in a host and providing for selection of transformant cells. The gene may provide for resistance to a cytotoxic agent, e.g. antibiotic, heavy metal, toxin, etc., complementation providing prototrophy to an auxotrophic host, viral immunity or the like. Depending upon the number of different host species the expression construct or components thereof are introduced, one or more markers may be employed, where different conditions for selection are used for the different hosts.

The manner in which the DNA construct is introduced into the plant host is not critical to this invention. Any method which provides for efficient transformation may be employed. Various methods for plant cell transformation include the use of Ti- or Ri-plasmids, microinjection, electroporation, liposome fusion, DNA bombardment or the like. In many instances, it will be desirable to have the construct bordered on one or both sides by T-DNA, particularly having the left and right borders, more particularly the right border. This is particularly useful when the construct uses *A. tumefaciens* or *A. rhizogenes* as a mode for transformation, although the T-DNA borders may find use with other modes of transformation.

Where the Agrobacterium is used for plant cell transformation, a vector may be used which may be introduced into the Agrobacterium host for homologous recombination with T-DNA or the Ti- or Ri-plasmid present in the Agrobacterium host. The Ti- or Ri-plasmid containing the T-DNA for recombination may be armed (capable of causing gall formation) or disarmed (incapable of causing gall formation), the latter being permissible, so long as the vir genes are present in the transformed host. The armed plasmid can give a mixture of normal plant cell and gall.

In some instances where Agrobacterium is used as the vehicle for transforming plant cells, the expression construct bordered by the T-DNA border(s) will be inserted into a broad host spectrum vector, there being broad host spectrum vectors described in the literature. Commonly used is pRK2 or derivatives thereof. See, for example, Ditta et al., *PNAS USA*, (1980) 77:7347–7351 and EPA 0 120 515, which are incorporated herein by reference. Included with the expression construct and the T-DNA will be one or more markers, which allow for selection of transformed Agrobacterium and transformed plant cells. A number of markers have been developed for use with plant cells, such as resistance to chloramphenicol, the aminoglycoside G418, hygromycin, or the like. The particular marker employed is not essential to this invention, one or another marker being preferred depending on the particular host and the manner of construction.

The expression constructs may be employed with a wide variety of plant life, particularly plant life involved in the production of vegetable oils. These plants include rapeseed, sunflower, safflower, cotton, Cuphea, soybean, and corn.

For transformation of plant cells using Agrobacterium, explants may be combined and incubated with the transformed Agrobacterium for sufficient time for transformation, the bacteria killed, and the plant cells cultured in an appropriate selective medium. Once callus forms, shoot formation can be encouraged by employing the appropriate plant hormones in accordance with known methods and the shoots transferred to rooting medium for regeneration of plants. The plants may then be grown to seed and the seed used to establish repetitive generations and for isolation of vegetable oils.

In addition, the safflower desaturase produced in accordance with the subject invention can be used in preparing antibodies for assays for detecting plant desaturase from other sources. The plant desaturase can also be used in conjunction with chloroplast lysates to enhance the production and/or modify the composition of the fatty acids prepared in vitro. The plant desaturase can also be used for studying the mechanism of fatty acid formation in plants and bacteria.

The invention now being generally described, it will be more readily understood by reference to the following examples which are included for purposes of illustration only and are not intended to limit the present invention.

EXAMPLES

Materials

Commercially available biological chemicals and chromatographic materials, including BSA, catalase (twice crystalized from bovine liver), spinach ferredoxin, ferredoxin-NADP$^+$ oxidoreductase (spinach leaf), NADPH, unlabeled fatty acids, DEAE-cellulose (Whatman DE-52) CNBr-activated Sepharose 4B, and octyl-Sepharose, and Reactive Blue Agarose are from Sigma (St. Louis, Mo.). Triethylamine, trichloroacetic acid, guanidine-HCl, and hydrazine-hydrate are also from Sigma. Proteolytic enzymes, including endoproteinases lysC, gluc, and aspN are sequencing grade enzymes obtained from Boehringer Mannheim (Indianapolis, Ind.). Organic solvents, including acetone, acetonitrile, methanol, ether and petroleum ether are purchased from J. T. Baker (Phillipsburg, N.J.); concentrated acids and sodium sulfate are also from J. T. Baker (Phillipsburg, N.J.). HPLC grade acetonitrile and trifluoracetic acid (TFA) are obtained from Burdick and Jackson (Muskegon, Mich.), and from Applied Biosystems (Foster City, Calif.), respectively. Radiochemicals, including [9,10(n)-$^3$H] oleic acid (10 mCi/μmol) and [$^3$H]-iodoacetic acid (64 Ci/mol) are from New England Nuclear (Boston, Mass.).

Phenacyl-8 Reagent (bromoacetophenone with a crown ether catalyst) used to prepare phenacyl esters of the fatty acids for analysis are from Pierce (Rockford, Ill.). C18 reversed-phase thin-layer chromatography plates are from Whatman (Clifton, N.J.).

Acyl carrier protein (ACP) and acyl-ACP synthase are isolated from *E. coli* strain K-12 as described by Rock and Cronan (Rock and Cronan, *Methods in Enzymol* (1981) 71:341–351 and Rock et al., *Methods in Enzymol.* (1981) 72:397–403). The *E. coli* is obtainable from Grain Processing (Iowa) as frozen late-logarithmic phase cells.

[9,10(n)-$^3$H] stearic acid is synthesized by reduction of [9,10(n)-$^3$H] oleic acid with hydrazine hydrate essentially as described by Johnson and Gurr (*Lipids* (1971) 6:78–84). [9,10(n)-$^3$H] oleic acid (2 mCi), supplemented with 5.58 mg unlabeled oleic acid to give a final specific radioactivity of 100 mCi/mmol, is dissolved in 2 ml of acetonitrile, acidified with 40 μl of glacial acetic acid, and heated to 55° C. Reduction is initiated with 100 μl of 60% (w/w) hydrazine hydrate; oxygen is bubbled through the mixture continuously. After each hour acetonitrile is added to bring the volume back to 2 ml and an additional 100 μl of hydrazine hydrate is added. At the end of 5 hr. the reaction is stopped by addition of 3 ml of 2M HCl. The reaction products are extracted with three 3-ml aliquots of petroleum ether and the combined ether extracts are washed with water, dried over sodium sulfate and evaporated to dryness. The dried reaction products are redissolved in 1.0 ml acetonitrile and stored at 20° C. The distribution of fatty acid products in a 15 μl aliquot is determined by preparation of phenacyl esters, which are then analyzed by thin layer chromatography on C-18 reverse phase plates developed with methanol:water::95:5 (v/v). Usually reduction to [9,10(n)-$^3$H]stearic acid is greater than 90%, a small amount of unreacted oleic acid may remain. The analysis is used to establish fraction of the total radioactivity that is present as stearate, and thereby to determine the exact substrate concentration in the enzyme assay.

Acyl-ACP substrates, including [9,10(n)-$^3$H] stearoyl-ACP are prepared and purified by the enzymatic synthesis procedure of Rock, Garwin, and Cronan (*Methods in Enzymol.* (1981) 72:397–403).

Acyl carrier protein was covalently bound to Sepharose 4B by reaction of highly purified ACP with CNBr-activated Sepharose 4B as described by McKeon and Stumpf (*J. Biol. Chem.* (1982) 257:12141–12147).

Example 1

In this example, an initial purification of safflower stearoyl-ACP desaturase, following the method of McKeon and Stumpf (*J. Biol. Chem.* (1982) 257:12141–12142), is described.

Assay: In each of the following steps, the presence of the enzyme is detected radiometrically by measuring enzyme-catalyzed release of tritium from [9,10(n)-$^3$H]stearoyl-ACP. Preparation of this substrate is described in "Materials" above.

The assay is performed by mixing 150 μl water, 5 ml dithiothreitol (100 mM, freshly prepared in water), 10 μl bovine serum albumin (10 mg/ml in water), 15 μl NADPH (25 mM, freshly prepared in 0.1 M Tricine-HCl, pH 8.2), 25 μl spinach ferredoxin (2 mg/ml Sigma Type III in water), 3 μl NADPH:ferredoxin oxidoreductase (2.5 units/ml from Sigma), and 1 μl bovine liver catalase (800,000 units/ml from Sigma); after 10 min at room temperature, this mixture is added to a 13×100 mm screw-cap test tube containing 250 μl sodium 1,4-piperazinediethanesulfonate (0.1 M, pH 6.0).

Finally, 10 μl of the sample to be assayed is added and the reaction is started by adding 30 μl of the substrate, [9,10 (n)-³H]stearoyl-ACP (100 μCi/μmol, 10 μM in 0.1 M sodium 1,4-piperazinediethanesulfonate, pH 5.8). After sealing with a cap, the reaction is allowed to proceed for 10 min. while shaking at 23° C. The reaction is terminated by addition of 1.2 ml of 5.8% tricholoracetic acid and the resulting precipitated acyl-ACP's are removed by centrifugation. The tritium released into the aqueous supernatant by the desaturase reaction is measured by liquid scintillation spectrometry.

Source tissue: Developing safflower seeds (*Carthamus tinctorius*) from greenhouse grown plants are harvested between 16 and 18 days after flowering, frozen in liquid nitrogen and stored at −70° C. until extracted.

Acetone Powder: Approximately 50 g of frozen safflower seeds are ground in liquid nitrogen and sieved to remove large seed coat pieces to provide a fine embryo powder. The powder is washed with acetone on a Buchner funnel until all yellow color is absent from the filtrate. The powder is then air dried and further processed as described below, or may be stored frozen for at least a year at −70° C. without loss of enzyme activity.

Acetone Powder Extract: The dried acetone powder is weighed and triturated with ten times its weight of 20 mM potassium phosphate, pH 6.8; the mixture is then centrifuged at 12,000×g for 20 minutes and decanted through a layer of Miracloth (Calbiochem, La Jolla, Calif.).

Ion Exchange Chromatography: The acetone powder extract is then applied to a DEAE-cellulose column (Whatman DE-52) (1.5×12 cm) equilibrated with 20 mM potassium phosphate, pH 6.8. The pass-through and a wash with one column-volume (20 ml) of buffer are pooled.

Affinity Chromatography: An affinity matrix for purification of the desaturase is prepared by reacting highly purified *E. coli* ACP, with CNBr-activated Sepharose 4B (Sigma). ACP (120 mg) is reduced by treatment with 1 mM dithiothreitol for 30 min on ice, and then desalted on Sephadex G-10 (Pharmacia) equilibrated with 0.1M sodium bicarbonate, pH 6.0. The treated ACP (20 ml, 6 mg/ml) is then mixed with 20 ml of CNBr-activated Sepharose 4B swollen in 0.1 M sodium bicarbonate, pH 7.0, and the mixture is allowed to stand at 4° C. for one day. The gel suspension is then centrifuged, washed once with 0.1M sodium bicarbonate, pH 7.0, and then treated with 40 ml 0.1M glycine, pH 8.0, for 4 hours at room temperature to block unreacted sites. The gel is then washed for five cycles with alternating 50-ml volumes of 0.5M NaCl in 0.1M sodium acetate, pH 4.0, and 0.5M NaCl in 0.1M sodium bicarbonate, pH 6.5, to remove noncovalently bound ligand. The gel is loaded into a column (1.5×11.2 cm) and equilibrated in 20 mM potassium phosphate, pH 6.8.

The combined fractions from the DE-52 column are applied to the column, which is subsequently washed with one column volume (20 ml) of the equilibration buffer, and then with 2.5 column volumes (50 ml) of 300 mM potassium phosphate, pH 6.8. Fractions are assayed for protein using the BCA Protein Assay Reagent (Pierce, Rockford, Ill.) to make sure that all extraneous protein has been eluted. Active stearoyl-ACP desaturase is eluted from the column with 600 mM potassium phosphate, pH 6.8. Active fractions are analyzed by polyacrylamide gel electrophoresis in sodium dodecyl sulfate (SDS-PAGE) on 0.75 mm thick 8×12 cm mini-gels according to the method of Laemmli (*Nature* (1970) 227:680). The running gel contains 10% acrylamide in a 30/0.8 ratio of acrylamide to cross-linker bis-acrylamide. Those fractions containing a predominant band at approximately 43 kD are pooled and stored frozen at −70° C. until final purification. The yield from 50 g of safflower seed tissue is is approximately 60 μg of protein as measured by amino acid analysis.

Further purification as described in Example 2 or Example 3 is then applied to the fractions pooled from the ACP-Sepharose column separation.

Example 2

In this example, a protocol for the final purification of safflower stearoyl-ACP desaturase is described. Safflower seeds are treated in accordance with Example 1.

Reverse-Phase HPLC: Fractions from the ACP-Sepharose column are pooled and applied to a Vydac C4 reverse-phase column (0.45×15 cm) equilibrated in 0.1% TFA, 7% acetonitrile. After a 10 min wash with 0.1% TFA, the column is eluted with a gradient of increasing acetonitrile (7%–70% v/v) in 0.1% TFA over a period of 45 min. The flow rate is 0.5 ml/min throughout. Eluting components are monitored by absorbance at 214 nm. Stearoyl-ACP desaturase elutes at about 42 min. (approximately 50% acetonitrile); the major contaminant protein remaining from ACP-affinity chromatography elutes at about 28 min. (approximately 30% acetonitrile). The substantially homogeneous stearoyl-ACP desaturase, which is no longer active, is identified by SDS-PAGE, in which it exhibits a single band corresponding to a molecular weight of approximately 43 kD. The quantity of desaturase protein in the sample may be determined by amino acid analysis.

Example 3

In this example, a protocol for the final purification of safflower stearoyl-ACP desaturase is described. Safflower seeds are treated in accordance with Example 1.

Reduction and Alkylation: Protein is precipitated out of the pooled fraction solutions recovered from the ACP-Sepharose column with 10% (w/v) trichloroacetic acid, washed with cold (−20° C.) acetone, and resuspended in 1 ml 500 mM Tris-HCl, pH 8.6, containing 6M guanidine-HCl, 10 mM EDTA, and 3.2 mM dithiothreitol. After 2 hours, 3.52 μmol [³H]-iodoacetic acid (64 μCi/pnol, New England Nuclear) is added, and the reaction is allowed to proceed at room temperature in the dark for 2 hours, at which time the reaction is terminated by addition of 1 μl (15 μmol) β-mercaptoethanol. The sample is then re-precipitated with 10% (w/v) trichloroacetic acid, and the pellet again washed with cold (−20° C.) acetone and resuspended in Laemmli's SDS-sample buffer (*Nature* (1970) 227:680).

SDS-Polyacrylamide Gel Electrophoresis: The resulting sample is boiled for 5 min. and then applied to a 1.5 mm thick, 8×12 cm, SDS-polyacrylamide mini-gel prepared as described by Laemmli, supra. The running gel contains 17.5% acrylamide in a 30:0.13 ratio of acrylamide to cross-linking bis-acrylamide. Separation is achieved by electrophoresis at 15 mA, for 2 hours at 4° C.

Blotting from SDS-gels to PVDF Membrane: Proteins are recovered from the gel by electroblotting at 5 mA/cm² to a four-layer sandwich of polyvinylidenedifluoride (PVDF) membrane for 2 h at 4° C. in a buffer containing 10 mM CAPS ("3-(cyclohexylaminol-1-propane-sulfonic acid"), pH 11. The membranes must be wetted in 50% methanol, prior to exposure to the blotting buffer. After blotting, the membrane layers are stained for 1–2 min. in 0.02% Coomassie Blue in 50% methanol, and then destained in 50% methanol. The desaturase is identified as a band corresponding to a molecular weight of about 43 kD; the major contaminant runs at or near the dye front of the gel corresponding to a molecular weight less than 20 kD.

The desaturase band on the PVDF membrane may be applied directly to the Edman sequencer (Applied Biosystems Model 477A) for determination of the N-terminal sequence of the intact protein, or for more extensive sequence determination, may be eluted from the membrane in 40% acetonitrile to recover pure desaturase in solution. Acetonitrile is removed from the eluted desaturase by evaporation on a Speed-Vac (Savant; Farmingdale, N.Y.), and the substantially homogeneous stearoyl-ACP desaturase is resuspended in an appropriate buffer for subsequent proteolytic digestion as described in Example 4. The quantity of desaturase protein present may be determined by amino acid analysis.

Alternatively, if the sample is to be digested with trypsin or gluc protease to generate peptides for amino acid sequence analysis, proteins may be electroblotted to nitrocellulose membranes and stained with Ponceaus or amido black.

Example 4

In this example, a method for the determination of the amino acid sequence of a plant stearoyl-ACP desaturase is described.

Reduction and Alkylation: Substantially homogenous stearoyl-ACP desaturase from Example 2 is reduced and alkylated with [$^3$H]-iodacetic acid as described in Example 3, except that the final acetone-washed pellet is resuspended in the appropriate buffer for subsequent proteolysis. Reduction and alkylation assures complete denaturation of the protein so that complete proteolysis can occur. The sample may be alkylated with radiolabeled iodoacetamide or with 4-vinylpyridine instead of [$^3$H]-iodacetic acid in substantially the same manner. Use of iodoacetic acid affords an alkylated sample with greater solubility, which is advantageous in subsequent sample manipulation.

Proteolysis: Substantially pure alkylated samples of stearoyl-ACP desaturase are digested with endoproteinase lysC. The sample is resuspended in 100 μl of 25 mM Tris-HCl, pH 8.8, containing 1 mM EDTA. Endoproteinase lysC is added to the sample in a protease/desaturase ratio of 1/50 (w/w). Digestion is allowed to proceed at room temperature for 8 hours, at which time another equal amount of protease is added. After 18 more hours, 1 μl of concentrated HCl is added to stop proteolysis, and the sample is applied directly to a Vydac C18 reverse-phase column (0.2×15 cm) equilibrated in 7% acetonitrile (v/v) in 0.1 mM sodium phosphate, pH 2.2. After washing for 20 min with the equilibration buffer, peptides are eluted with a gradient in acetonitrile (7–70%, v/v) over 120 min. Flow rate is 50 μl/min, throughout. Eluting components are monitored by absorbance at 214 nm, and individual peptide peaks are collected as separate fractions. The peptide fractions are further purified by application to a second Vydac C18 reverse-phase column (0.2×15 cm) equilibrated in 7% (v/v) acetonitrile in 0.1% (v/v) trifluoroacetic acid. Again, after a 20 min wash with equilibration buffer, the substantially pure peptides are eluted with a gradient (7–70%, v/v) of acetonitrile in 0.1% trifluoroacetic acid over 120 min. The flow rate is 50 μl/min, throughout. Eluting components are monitored by absorbance at 214 nm, and individual peptide peaks are collected as separate fractions. These substantially pure peptides are applied directly to the Edman sequencer (Applied Biosystems, Model 477A) for amino acid sequence analysis. Alternatively, peptide fraction from the first HPLC purification in phosphate buffer, or from a single chromatography step in trifluoroacetic acid buffer, may be applied directly to the sequencer, but these fractions, in many cases, are not substantially pure and yield mixed or ambiguous sequence information.

Other proteases may be used to digest desaturase, including but not limited to trypsin, gluc, and aspN. While the individual digest buffer conditions may be different, the protocols for digestion, peptide separation, purification, and sequencing are substantially the same as those outlined for the digestion with lysC. Fragments generated from these digestion steps are presented in FIG. 1. Alternatively, desaturase may be digested chemically using cyanogen bromide (Gross *Methods Enzymol* (1967) 11:238–255 or Gross and Witkop *J. Am. Chem. Soc.* (1961) 83:1510), hydroxylamine (Bornstein and Balian *Methods Enzymol.* (1977) 47:132–745), iodosobenzoic acid (Inglis *Methods Enzymol.* (1983) 91:324–332), or mild acid (Fontana et al., *Methods Enzymol.* (1983) 91:311–317), as described in the respective references.

Example 5

In this example, the preparation of a plant stearoyl-ACP desaturase cDNA bank, using the methods as described in Alexander, et al. (*Methods in Enzymology* (1987) 154:41–64) is described.

A plant embryo cDNA library may be constructed from poly(A)+RNA isolated from safflower embryos collected at 14–17 days post-anthesis. Poly(A)+ RNA is isolated from polyribosomes by a method initially described by Jackson and Larkins (*Plant Physiol.* (1976) 57:5–10) as modified by Goldberg et al. (*Developmental Biol.* (1981) 83:201–217).

The plasmid cloning vector pCGN1703, derived from the commercial cloning vector Bluescribe M13- (Stratagene Cloning Systems; San Diego, Calif.), is made as follows. The polylinker of Bluescribe M13- is altered by digestion with BamHI, treatment with mung bean endonuclease, and blunt-end ligation to create a BamHI-deleted plasmid, pCGN1700. pCGN1700 is digested with EcoRI and SstI (adjacent restriction sites) and annealed with synthetic complementary oligonucleotides having the sequences 5' CGGATCCACTGCAGTCTAGAGGGCCCGGGA 3' and 5' AATTTCCCGGGCCCTCTAGACTGCAGTG-GATCCGAGCT 3'. These sequences are inserted to eliminate the EcoRI site, move the BamHI site onto the opposite side of the SstI (also, sometimes referred to as "SacI" herein) site found in Bluescribe, and to include new restriction sites PstI, XbaI, ApaI, SmaI. The resulting plasmid pCGN1702, is digested with HindIII and blunt-ended with Klenow enzyme; the linear DNA is partially digested with PvuII and ligated with T4 DNA ligase in dilute solution. A transformant having the lac promoter region deleted is selected (pCGN1703) and is used as the plasmid cloning vector.

Briefly, the cloning method for cDNA synthesis is as follows. The plasmid cloning vector is digested with SstI and homopolymer T-tails are generated on the resulting 3'-overhang sticky-ends using terminal deoxynucleotidyl transferase. The tailed plasmid is separated from undigested or un-tailed plasmid by oligo(dA)-cellulose chromatography. The resultant vector serves as the primer for synthesis of cDNA first strands covalently attached to either end of the vector plasmid. The cDNA-mRNA-vector complexes are treated with terminal transferase in the presence of deoxyguanosine triphosphate, generating G-tails at the ends of the cDNA strands. The extra cDNA-mRNA complex, adjacent to the BamHI site, is removed by BamHI digestion, leaving a cDNA-mRNA-vector complex with a BamHI sticky-end at one end and a G-tail at the other. This complex is cyclized using the annealed synthetic cyclizing linker, 5'-GATCCGCGGCCGCGAATTCGAGCTCCCCCCCC-CC-3' and 3'-GCGCCGGCGCTTAAGCTCGA-5' which has a BamHI sticky-end and a C-tail end. Following ligation and repair the circular complexes are transformed into *E. coli* strain DH5α(BRL; Gaithersburg, Md.) to generate the cDNA library. The safflower embryo cDNA bank contains between $3 \times 10^6$ and $5 \times 10^6$ clones with an average cDNA insert size of approximately 1000 base pairs.

Probe production Including PCR Reactions

Two regions of amino acid sequence (Example 4) with low codon degeneracy are chosen from opposite ends of peptide sequence "Fragment F2" for production of a probe for the plant desaturase cDNA. Two sets of mixed oligonucleotides are designed and synthesized for use as forward and reverse primers, respectively, in the polymerase chain reaction (Saiki et al., *Science* (1985) 230:1350–1354; Oste, *Biotechniques* (1988) 6:162–167). See, FIG. 3. All oligonucleotides are synthesized on an Applied Biosystems 380A DNA synthesizer.

Probes to safflower stearoyl-ACP desaturase may be prepared using the peptide sequence "Fragment 2" identified in FIG. 1. Four types of forward primers were synthesized and labeled 13-1, 13-2, 13-3, and 13-4. Two groups of reverse primers were synthesized and designated 13-5A and 13-6A. The primer sequences are shown in FIG. 3. These oligonucleotide groups have a redundancy of 64 or less and contain either 20 or 17 bases of coding sequence along with flanking restriction site sequences for HindIII or EcoRI. Based on the intervening amino acid sequence between the primer regions on peptide "Fragment 2" the PCR product is expected to contain 107 base pairs.

Polymerase chain reaction is performed using the cDNA library DNA as template and the possible eight combinations of the four forward and two reverse oligonucleotides as primers in a Perkin-Elmer/Cetus DNA Thermal Cycler (Norwalk, Conn.) thermocycle file 1 min. 94° C., 2 min. 42° C., 2 min rise from 42°–72° C. for 30 cycles, followed by the step cycle file without step rises, 1 min. 94° C., 2 min. 42° C., 3 min. 72° C. with increasing 15 sec extensions of the 72° C. step for 10 cycles, and a final 10 min. 72° C. extension.

The product of the 13-4 forward primer and the 13-5A reverse primer reaction was ethanol precipitated and then digested with HindIII and EcoRI, the resulting fragment was subcloned into pUC8 (Vieira and Messing, *Gene* (1982) 19:259–268). Minipreparation DNA (Maniatis et al., *Molecular Cloning: A Laboratory Manual* (1982) Cold Harbor Laboratory, New York) of one clone was sequenced by Sanger dideoxy sequencing (Sanger et al., *Proc. Nat. Acad. Sci. USA* (1977) 74:5463–5467) using the M13 universal and reverse primers. Translation of the resulting DNA sequence results in a peptide sequence that exactly matches the amino acid sequence in peptide "Fragment F2".

An exact 50 base oligonucleotide designated DESAT-50 is synthesizing to match the sequence of the PCR reaction product from the first valine residue to the last tyrosine residue.

The probe DSAT-50 5'-GTAAGTAGGTAGGGCTTCCTCTGTAATCATATCT-CCAACCAAAACAACAA -3' is used to probe the safflower embryo cDNA library.

Library Screen

The safflower embryo cDNA bank is moved into the cloning vector lambda gt10 (Stratagene Cloning Systems) by digestion of total cDNA with EcoRI and ligation to lambda gt10 DNA digested with EcoRI. The titer of the resulting library was $\sim 5 \times 10^5$/ml. The library is then plated on *E. coli* strain C600 (Huynh, et al., *DNA Cloning* Vol. 1 Eds. Glover D. M. IRL Press Limited: Oxford England, pp. 56, 110) at a density of 5000 plaques/150 mm NZY ("NZYM" as defined in Maniatis et al. supra) agar plate to provide over 45,000 plaques for screening. Duplicate lifts are taken of the plaques using NEN Colony Plaque Screen filters by laying precut filters over the plates for ~1 minute and then peeling them off. The phage DNA is immobilized by floating the filters on denaturing solution (1.5M NaCl, 0.05M NaOH) for 1 min., transferring the filters to neutralizing solution (1.5M NaCl, 0.5M Tris-HCl pH 8.0) for 2 min. and then to 2xSSC (1xSSC=0.15M NaCl; 0.015M Na citrate) for 3 min., followed by air drying. The filters are hybridized with $^{32}$P end-labeled DSAT-50 oligonucleotide (BRL 5' DNA Terminus Labeling System) by the method of Devlin et al., (*DNA* (1988) 7:499–807) at 42° C. overnight, and washed for 30 min. at 50° C. in 2xSSC, 0.5% SDS and then twice for 20 min. each at 50° C. in 0.1XSSC, 0.5% SDS. Filters are exposed to X-ray film at -70° C. with a Dupont Cronex intensifying screen for 48 hours.

Clones are detected by hybridization with the DSAT-50 oligonucleotide and plaque purified. The complete nucleotide sequence of the cDNA insert of a clone, pCGN2754, and a partial restriction map thereof are presented in FIGS. 2 and 4, respectively. The cDNA insert includes 1533 bases plus a poly(A) track at the 3' end of 100–200 bases. The open reading frame for stearoyl-ACP desaturase begins at the first ATG (nucleotide 106) from the 5' end and stops at nucleotide 1294. The open reading frame includes a 33 amino acid transit peptide not found in the amino acid sequence of the mature protein. The N-terminus of the protein begins at the alanine immediately following the NcoI site (nucleotide 202) indicating the site of the transit peptide processing.

Example 6

In this example, expression of safflower stearoyl-ACP desaturase in a prokaryote is described.

Desaturase Expression Construct in *E. coli*

A plasmid for expression of stearoyl-ACP desaturase activity in *E. coli* is constructed as follows. The desaturase cDNA clone pCGN2754 is digested with HindIII and SalI and ligated to pCGN2016 (a chloramphenicol resistant version of Bluescript KS-) digested with HindIII and XhoI. The resulting plasmid is pCGN1894.

pCGN2016 is prepared by digesting pCGN565 with HhaI, and the fragment containing the chloramphenicol resistance gene is excised, blunted by use of mung bean nuclease, and inserted into the EcoRV site of Bluescript KS- (Stratagene: La Jolla, Calif.) to create pCGN2008. The choramphenicol resistance gene of pCGN2008 is removed by EcoRI/HindIII digestion. After treatment with Klenow enzyme to blunt the ends, the fragment is ligated to DraI digested Bluescript KS-. A clone that has the DraI fragment containing ampicillin resistance replaced with the chloramphenicol resistance is chosen and named pCGN2016.

pCGN565 is a cloning vector based on pUC12-cm (K. Buckley Ph.D. Thesis, Regulation and expression of the phi X174 lysis gene, University of California, San Diego, 1985), but contains pUC18 linkers (Yanisch-Perron, et al., *Gene* (1985) 53:103–119).

The fragment containing the mature coding region of the stearoyl-ACP desaturase, 3'-noncoding sequences and poly (A) tails is subcloned from pCGN1894 digested with Nco1 and Asp718 into pUC120, an *E. coli* expression vector based on pUC118 (Vieria and Messing, *Methods in Enzymology* (1987) 153:3–11) with the lac region inserted in the opposite orientation and an NcoI site at the ATG of the lac peptide (Vieira, J. PhD. Thesis, University of Minnesota, 1988). The *E. coli* desaturase expression plasmid is designated pCGN3201. The desaturase sequences are inserted such that they are aligned with the lac transcription and translation signals.

Expression of Stearoyl ACP Desaturase in *E.coli*

Single colonies of *E. coli* strain 7118 (Maniatis et al., supra) containing pUC120 or pCGN3201 are cultured in 80 mls each of ECLB broth, 300 mg/L penicillin. The cells are induced by the addition of 1 mM IPTG. Cells are grown overnight (18 hrs) at 37° C.

Eighty mls of overnight cultures of *E. coli* (induced and uninduced) containing pUC120 or pCGN3201 are centrifuged at 14,800×g for 15 min. The pelleted cells are resuspended in 3 mls 20 mM phosphate buffer, pH 6.8. Resuspended cells were broken in a french press at 16,000 psi. Broken cell mixtures are centrifuged 5000×g for 5 min. 100 ul of each supernatant is applied to a G-25 Sephadex gel filtration centrifugal column (Boehringer Mannheim Biochemicals), equilibrated in 20 mM phosphate buffer pH 6.8. Columns are spun for 4 min at 5000×g. Effluent was collected and used as enzyme source in the desaturase assay.

Stearoyl-ACP desaturase activity is assayed as described in Example 1. Both pUC120-containing, IPTG-induced cells and uninduced cells do not express detectable stearoyl-ACP desaturase activity. The pCGN3201 IPTG-induced extract contains 8.22 nmol/min of desaturase activity. pCGN3201 uninduced extracts contains 6.45 nmol/min of activity. The pCGN3201 IPTG-induced extract shows 21.5% more activity than the uninduced pCGN3201 extract.

Detection of Induced Protein in *E. coli*

Extracts of overnight cultures of *E. coli* strain 7118 (Maniatis et al. supra ) containing pCGN3201 or pUC120 grown in ECLB containing 300 mg/L penicillin induced with 1 mM IPTG are prepared as follows. 1.5 ml of overnight culture grown shaking at 37° C. are pelleted in Eppendorf tubes for 10 min at 10–13,000 µg. Pellets are. resuspended in 150 ul SDS sample buffer (0.05M Tris-HCl, pH 6.8, 1% SDS, 5% β-mercaptoethanol, 10% glycerol and 0.005% bromophenol blue) and boiled for 10 min. 25 µl of each sample are electrophoresed on a 10% polyacrylamide gel (Laemmli, *Nature* (1970) 227:680) at 25 mA for 5 hours. Gels are stained in 0.05% Coomassie Brilliant Blue, 25% isopropanol and 10% acetic acid and destained in 10% acetic acid and 10% isopropanol. A band is detected at just below the 43,000 MW protein marker (SDS PAGE standard, Low molecular weight, BioRad, Richmond Calif.) in the pCGN3201 extracts that is not present in the pUC120 extracts. This is the approximate molecular weight of mature desaturase protein.

Example 7

In this example, the preparation of an ACP expression cassette containing safflower stearoyl-ACP desaturase in a binary vector suitable for plant transformation is described.

ACP Expression Cassette

An expression cassette utilizing 5'-upstream sequences and 3'-downstream sequences obtainable from *B. campestris* ACP gene can be constructed as follows.

A 1.45 kb XhoI fragment of Bcg 4-4 (FIG. 6) containing 5'-upstream sequences is subcloned into the cloning/sequencing vector Bluescript+ (Stratagene Cloning Systems, San Diego, Calif.). The resulting construct, pCGN1941, is digested with XhoI and ligated to a chloramphenicol resistant Bluescript M13+ vector, pCGN2015 digested with XhoI. pCGN2015 is prepared as described for pCGN2016 (See, Example 6) except that the EcoRI/HindIII "chloramphenicol" fragment isolated from pCGN2008 is ligated with the 2273 bp fragment of Bluescript KS⁺ (Stratagene; LaJolla, Calif.) isolated after digestion with DraI. This alters the antibiotic resistance of the plasmid from penicillin resistance to chloramphenicol resistance. The chloramphenicol resistant plasmid is pCGN1953.

3'-sequences of Bcg 4-4 are contained on an SstI/BglII fragment cloned in the SstI/BamHI sites of M13 Bluescript+ vector. This plasmid is named pCGN1940. pCGN1940 is modified by in vitro site-directed mutagenesis (Adelman et al., *DNA* (1983) 2:183–193) using the synthetic oligonucleotide 5'-CTTAAGAAGTAACCCGGGCTGCAGTTTTAGTATT-AAGAG-3' to insert SmaI and PstI restriction sites immediately following the stop codon of the reading frame for the ACP gene 18 nucleotides from the SstI site. The 31-noncoding sequences from this modified plasmid, pCGN1950, are moved as a PsI-SmaI fragment into pCGN1953 cut with PstI and SmaI. The resulting plasmid pCGN1977 comprises the ACP expression cassette with the unique restriction sites EcoRV, EcoRI and PstI available between the 1.45 kb 5' and 1.5 kb of 3'-noncoding sequences for the cloning of genes to be expressed under regulation of these ACP gene regions.

Stearoyl Desaturase Expression in Plants

Desaturase cDNA sequences from pCGN2754 are inserted in the ACP expression cassette, pCGN1977, as follows. pCGN2754 is digested with HindIII (located 160 nucleotides upstream of the start codon) and Asp718 located in the polylinker outside the poly(A) tails. The fragment containing the coding region for desaturase was blunt-ended using DNA polymerase I and ligated to pCGN1977 digested with EcoRV. A clone containing the desaturase sequences in the sense orientation with respect to the ACP promoter is selected and called pCGN1895. The fragment containing the pCGN1895 expression sequences ACP 5'/desaturase/ACP 3' is cloned into a binary vector pCGN1557 (described below) for Agrobacterium transformation by digestion with Asp718 and XbaI and ligation to pCGN1557 digested with Asp718 and XbaI. The resulting binary vector is called pCGN1898.

pCGN1898 is transformed into *Agrobacterium tumefaciens* strain EHA101 (Hood, et al., *J. Bacteriol.* (1986) 168:1291–1301) as per the method of Holsters, et al., *Mol. Gen. Genet.* (1978) 163:181–187.

Construction of pCGN1557 pCGN1557 (McBride and Summerfelt, *Plant Molecular Biology* (1990) 14(2):269–276) is a binary plant transformation vector containing the left and right T-DNA borders of *Agrobacterium tumefaciens* octopine Ti-plasmid pTiA6 (Currier and Nester, supra, the gentamycin resistance gene of pPh1JI (Hirsch and Beringer, supra), an *Agrobacterium rhizogenes* Ri plasmid origin of replication from pLJbB11 (Jouanin et al., supra), a 35S promoter-kanR-tml3' region capable of conferring kanamycin resistance to transformed plants, a ColE1 origin of replication from pBR322 (Bolivar et al., supra), and a lacZ' screenable marker gene from pUC18 (Yanish-Perron et al., supra).

There are three major intermediate constructs used to generate pCGN1557:

pCGN1532 (see below) contains the pCGN1557 backbone, the pRi plasmid origin of replication, and the ColE1 origin of replication.

pCGN1546 (see below) contains the CaMV35S5'-kan$^R$-tml3' plant selectable marker region.

pCGN1541b (see below) contains the right and left T-DNA borders of the *A. tumefaciens* octopine Ti-plasmid and the lacZ' region from pUC19.

To construct pCGN1557 from the above plasmids, pCGN1546 is digested with XhoI, and the fragment containing the CaMV 35S5'-kan$^R$-tml3' region is cloned into the XhoI site of pCGN1541b to give the plasmid pCGN1553, which contains T-DNA/left border/CaMV 35S5'-kan$^R$-tml3'/lacZ'/T-DNA left border. pCGN1553 is digested with BglII, and the fragment containing the T-DNA/left border/CaMV35S5'-kan$^R$-tml3'/lacZ'/T-DNA left border region is ligated into BamHI-digested pCGN1532 to give the complete binary vector, pCGN1557.

pCGN1532

The 3.5 kb EcoRI-PstI fragment containing the gentamycin resistance gene is removed from pPhlJI (Hirsch and Beringer, *Plasmid* (1984) 12:139–141) by EcoRI-PstI digestion and cloned into EcoRI-PstI digested pUC9 (Vieira and Messing, *Gene* (1982) 19:259–268) to generate pCGN549. HindIII-PstI digestion of pCGN549 yields a 3.1 kb fragment bearing the gentamycin resistance gene, which is made blunt ended by the Klenow fragment of DNA polymerase I and cloned into PvuII digested pBR322 (Bolivar et al., *Gene* (1977) 2:95–113) to create pBR322Gm. pBR322Gm is digested with DraI and SphI, treated with Klenow enzyme to create blunt ends, and the 2.8 kb fragment cloned into the Ri origin-containing plasmid pLJbB11 (Jouanin et al., *Mol. Gen. Genet.* (1985) 201:370–374) which has been digested with ApaI and made blunt-ended with Klenow enzyme, creating pLHbB11Gm. The extra ColE1 origin and the kanamycin resistance gene are deleted from pLHbB11Gm by digestion with BamHI followed by self closure to create pGmB11. The HindII site of pGmB11 is deleted by HindIII digestion followed by treatment with Klenow enzyme and self closure, creating pGmB11-H. The PstI site of pGmB11-H is deleted by PstI digestion followed by treatment with Klenow enzyme and self closure, creating pCGN1532.

Construction of pCGN1546

The 35S promoter-tml3' expression cassette, pCGN986, contains a cauliflower mosaic virus 35S (CaMV35) promoter and a T-DNA tml 3'-region with multiple restriction sites between them. pCGN986 is derived from another cassette, pCGN206, containing a CaMV35S promoter and a different 3' region, the CaMV region VI 3'-end. The CaMV 35S promoter is cloned as an AluI fragment (bp 7144–7734) (Gardner et. al., *Nucl. Acids Res.* (1981) 9:2871–2888) into the HincII site of M13mp7 (Messing, et. al., *Nucl. Acids Res.* (1981) 9:309–321) to create C614. An EcoRI digest of C614 produced the EcoRI fragment from C614 containing the 35S promoter which is cloned into the EcoRI site of pUC8 (Vieira and Messing, *Gene* (1982) 19:259) to produce pCGN147.

pCGN148a containing a promoter region, selectable marker (KAN with 2 ATG's) and 3' region, is prepared by digesting pCGN528 with BglII and inserting the BamHI-BglII promoter fragment from pCGN147. This fragment is cloned into the BglII site of pCGN528 so that the BglII site is proximal to the kanamycin gene of pCGN528.

The shuttle vector used for this construct pCGN528, is made as follows: pCGN525 is made by digesting a plasmid containing Tn5 which harbors a kanamycin gene (Jorgenson et. al., *Mol. Gen. Genet.* (1979) 177:65) with HindIII-BamHI and inserting the HindIII-BamHI fragment containing the kanamycin gene into the HindIII-BamHI sites in the tetracycline gene of pACYC184 (Chang and Cohen, *J. Bacteriol.* (1978) 134:1141–1156). pCGN526 was made by inserting the BamHI fragment 19 of pTiA6 (Thomashow et. al., *Cell* (1980) 19:729–739), modified with XhoI linkers inserted into the SmaI site, into the BamHI site of pCGN525.

pCGN528 is obtained by deleting the small XhoI fragment from pCGN526 by digesting with XhoI and religating. pCGN149a is made by cloning the BamHI-kanamycin gene fragment from pMB9KanXXI into the BamHI site of pCGN148a. pMB9KanXXI is a pUC4K variant (Vieira and Messing, *Gene* (1982) 19:259–268) which has the XhoI site missing, but contains a functional kanamycin gene from Tn903 to allow for efficient selection in Agrobacterium.

pCGN149a is digested with HindIII and BamHI and ligated to pUC8 digested with HindIII and BamHI to produce pCGN169. This removes the Tn903 kanamycin marker. pCGN565 (see pCGN2016 description) and pCGN169 are both digested with HindIII and PstI and ligated to form pCGN203, a plasmid containing the CaMV 35S promoter and part of the 5'-end of the Tn5 kanamycin gene (up to the PstI site, Jorgenson et. al., (1979), supra). A 3'-regulatory region is added to pCGN203 from pCGN204 (an EcoRI fragment of CaMV (bp 408–6105) containing the region VI 3' cloned into pUC18 (Yanisch-Perron, et al., *Gene* (1985) 33:103–119) by digestion with HindIII and PstI and ligation. The resulting cassette, pCGN206, is the basis for the construction of pCGN986.

The pTiA6 T-DNA tml 3'-sequences are subcloned from the Bam19 T-DNA fragment (Thomashow et al., (1980) supra) as a BamHI-EcoRI fragment (nucleotides 9062 to 12,823, numbering as in Barker et al., *Plant Mol. Biol.* (1982) 2:335–350) and combined with the pACYC184 (Chang and Cohen (1978), supra) origin of replication as an EcoRI-HindIII fragment and a gentamycin resistance marker (from plasmid pLB41), obtained from D. Figurski) as a BamHI-HindIII fragment to produce pCGN417.

The unique SmaI site of pCGN417 (nucleotide 11,207 of the Bam19 fragment) is changed to a SacI site using linkers and the BamHI-SacI fragment is subcloned into pCGN565 to give pCGN971. The BamHI site of pCGN971 is changed to an EcoRI site using linkers. The resulting EcoRI-SacI fragment containing the tml 3' regulatory sequences is joined to pCGN206 by digestion with EcoRI and SacI to give pCGN975. The small part of the Tn5 kanamycin resistance gene is deleted from the 3'-end of the CaMV 35S promoter by digestion with SalI and BglII, blunting the ends and ligation with SalI linkers. The final expression cassette pCGN986 contains the CaMV 35S promoter followed by two SalI sites, an XbaI site, BamHI, SmaI, KpnI and the tml 3' region (nucleotides 11207–9023 of the T-DNA).

The 35S promoter-tml 3' expression cassette, pCGN986 is digested with HindIII. The ends are filled in with Klenow polymerase and XhoI linkers added. The resulting plasmid is called pCGN986X. The BamHI-SacI fragment of pBRX25 (see below) containing the nitrilase gene is inserted into BamHI-SacI digested pCGN986X yielding pBRX66.

Construction of pBRX25 is described in U.S. Pat. No. 4,810,648, which is hereby incorporated by reference. Briefly, the method is as follows: The nucleotide sequence of a 1212-bp PstI-HincII DNA segment encoding the bromoxynil-specific nitrilase contains 65-bp of 5' untranslated nucleotides. To facilitate removal of a portion of these excess nucleotides, plasmid pBRX9 is digested with PstI, and treated with nuclease Bal31. BamHI linkers are added to the resulting ends. BamHI-HincII fragments containing a functional bromoxynil gene are cloned into the BamHI-SmaI sites of pCGN565. The resulting plasmid, pBRX25, contains only 11 bp of 5' untranslated bacterial sequence.

pBRX66 is digested with PstI and EcoRI, blunt ends generated by treatment with Klenow polymerase, and XhoI linkers added. The resulting plasmid pBRX68 now has a tml 3' region that is approximately 1.1 kb. pBRX68 is digested with SalI and SacI, blunt ends generated by treatment with Klenow polymerase and EcoRI linkers added. The resulting plasmid, pCGN986XE is a 35S promoter - tml 3' expression cassette lacking the nitrilase gene.

The Tn5 kanamycin resistance gene is then inserted into pCGN986XE. The 1.0 kb EcoRI fragment of pCGN1536 (see pCGN1547 description) is ligated into pCGN986XE digested with EcoRI. A clone with the Tn5 kanamycin resistance gene in the correct orientation for transcription and translation is chosen and called pCGN1537b. The 35S promoter $Kan^R$-tml 3' region is then transferred to a chloramphenical resistant plasmid backbone. pCGN786, (a pUC-CAM based vector with the synthetic oligonucleotide 5' GGAATTCGTCGACAGATCTCTGCAGCTC-GAGGGATCCAAGCTT 3' containing the cloning sites EcoRI, SalI, BglII, PstI, XhoI, BamHI, and HindIII inserted into pCGN566, pCGN566 contains the EcoHI-HindIII linker of pUC18 inserted into the EcoKI-HindIII sites of pUC13-cm (K. Buckler (1985) supra)) is digested with XhoI and the XhoI fragment of pCGN1537b containing the 35S promoter—$Kan^R$-tml 3' region is ligated in. The resulting clone is termed pCGN1546.

pCGN1541b pCGN565RBα2X (see below) is digested with BglII and XhoI, and the 728bp fragment containing the T-DNA right border piece and the lacZ' gene is ligated with BglII-XhoI digested pCGN65ΔKX-S+K (see below), replacing the BglII-XhoI right border fragment of pCGN65ΔKX-S+K. The resulting plasmid, pCGN65α2X contains both T-DNA borders and the lacZ' gene. The ClaI fragment of pCGN65α2X is replaced with an XhoI site by digesting with ClaI blunting the ends using the Klenow fragment, and ligating with XhoI linker DNA, resulting in plasmid pCGN65α2XX. pCGN65α2XX is digested with BglII and EcoRV, treated with the Klenow fragment of DNA polymerase I to create blunt ends, and ligated in the presence of BglII linker DNA, resulting in pCGN65α2XX'. pCGN65α2XX' is digested with BglII and ligated with BglII digested pCGN1538 (see below), resulting in pCGN1541a, which contains both plasmid backbones. pCGN1541a is digested with XhoI and religated. Ampicillin resistant, chlormaphenicol sensitive clones are chosen, which lack the pACYC184-derived backbone, creating pCGN1541b.

pCGN1538 is generated by digesting pBR322 with EcoRI and PvuII, treating with Klenow to generate blunt ends, and ligating with BglII linkers. pCGN1538 is ampicillin resistant, tetracycline sensitive.

pCGN65ΔKX-S+K pCGN501 is constructed by cloning a 1.85 kb EcoRI-XhoI fragment of pTiA6 (Currier and Nester, *J. Bact.* (1976) 126:157–165) containing bases 13362–15208 (Barker et al., *Plant Mo. Biol.* (1983) 2:335–350) of the T-DNA (right border), into EcoRI-SalI digested M13mp9 (Vieira and Messing, *Gene* (1982) 19:259–268). pCGN502 is constructed by cloning a 1.6 kb HindIII-SmaI fragment of pTiA6, containing bases 602–2212 of the T-DNA (left border), into HindIII-SmaI digested M13mp9. pCGN501 and pCGN502 are both digested with EcoRI and HindIII and both T-DNA-containing fragments cloned together into HindIII digested pUC9 (Vieira and Messing, *Gene* (1982) 19:259–268) to yield pCGN503, containing both T-DNA border fragments. pCGN503 is digested with HindIII and EcoRI and the two resulting HindIII-EcoRI fragments (containing the T-DNA borders) are cloned into EcoRI digested pHC79 (Hohn and Collins, *Gene* (1980) 11:291–298) to generate pCGN518. The 1.6 kb KpnI-EcoRI fragment from pCGN518, containing the left T-DNA border, is cloned into KpnI-EcoRI digested pCGN565 to generate pCGN580. The BamHIII-BglII fragment of pCGN580 is cloned into the BamHI site of pACYC*184* (Chang and Cohen, *J. Bacteriol.* (1978) 134:1141–1156) to create pCGN51. The 1.4 kb BamHI-SphI fragment of pCGN60 containing the T-DNA right border fragment, is cloned into BamHI-SphI digested pCGN51 to create pCGN65, which contains the right and left T-DNA borders.

pCGN65 is digested with KpnI and XbaI, treated with Klenow enzyme to create blunt ends, and ligated in the presence of synthetic BglII linker DNA to create pCGN65ΔKX. pCGN65ΔKX is digested with SalI, treated with Klenow enzyme to create blunt ends, and ligated in the presence of synthetic XhoI linker DNA to create pCGN65ΔKX-S+X.

pCGN565RBα2X pCGN451 (see below) is digested with HpaI and ligated in the presence of synthetic SphI linker DNA to generate pCGN55. The XhoI-SphI fragment of pCGN55 (bp 13800–15208, including the right border, of *Agrobacterium tumefaciens* T-DNA; (Barker et al., *Gene* (1977) 2:95–113) is cloned into SalI-SphI digested pUC19 (Yanisch-Perron et al., *Gene* (1985) 53:103–119) to create pCGN60. The 1.4 kb HindIII-BamHI fragment of pCGN60 is cloned into HindIII-BamHI digested pSP64 (Promega, Inc.) to generate pCGN1039. pCGN1039 is digested with SmaI and NruI (deleting bp 14273–15208; (Barker et al., *Gene* (1977) 2:95–113) and ligated in the presence of synthetic BglII linker DNA creating pCGN1039ΔNS. The 0.47 kb EcoRI-HindIII fragment of pCGN1039ΔNS is cloned into EcoRI-HindIII digested pCGN565 to create pCGN565RB. The HindIII site of pCGN565RB is replaced with an XhoI site by digesting with HindIII, treating with Klenow enzyme, and ligating in the presence of synthetic XhoI linker DNA to create pCGN565RB-H+X.

pUC18 (Norrander et al., *Gene* (1983) 26:101–106) is digested with HaeII to release the lacZ' fragment, treated with Klenow enzyme to create blunt ends, and the lacZ'-containing fragment ligated into pCGN565RB-H+X, which had been digested with AccI and SphI and treated with Klenow enzyme in such a orientation that the lacZ' promoter is proximal to the right border fragment; this construct, pCGN565RBα2x is positive for lacZ' expression when plated on an appropriate host and contains bp 13990–14273 of the right border fragment (Barker et al., *Plant Mo. Biol.* (1983) 2:335–350) having deleted the AccI-SphI fragment (bp 13800–13990).

pCGN451 pCGN451 contains an ocs5'-ocs3' cassette, including the T-DNA right border, cloned into a derivative of pUC8 (Vieira and Messing, supra). The modified vector is derived by digesting pUC8 with HincII and ligating in the presence of synthetic linker DNA, creating pCGN416, and then deleting the EcoRI site of pCGN416 by EcoRI digestion followed by treatment with Klenow enzyme and self-ligation to create pCGN426.

The ocs5'-ocs3' cassette is created by a series of steps from DNA derived from the octopine Ti-plasmid pTiA6 (Currier and Nester, supra). To generate the 5' end, which includes the T-DNA right border, an EcoRI fragment of pTiA6 (bp 13362–16202 (the numbering is by Barker, et al., (*Plant Mol. Bio* (1983) 2:335–350) for the closely related Ti plasmid pTil5955)) is removed from pVK232 (Knauf and Nester, *Plasmid* (1982) 8:45) by EcoRI digestion and cloned into EcoRI digested pACYC184 (Chang and Cohen, supra) to generate pCGN15.

The 2.4 kb BamHI-EcoRI fragment (bp 13774–16202) of pCGN15 is cloned into EcoRI-BamHI digested pBR322

(Bolivar, et al., supra) to yield pCGN429. The 412 bp EcoRI-BamHI fragment (bp 13362–13772) of pCGN15 is cloned into EcoRI-BamHI digested pBR322 to yield pCGN407. The cut-down promoter fragment is obtained by digesting pCGN407 with XmnI (bp 13512), followed by resection with Bal31 exonuclease, ligation of synthetic EcoRI linkers, and digestion with BamHI. Resulting fragments of approximately 130 bp are gel purified and cloned into M13mp9 (Vieira and Messing, supra) and sequenced. A clone, I-4, in which the EcoRI linker has been inserted at bp 1362 between the transcription initiation point and the translation initiation codon is identified by comparison with the sequence of de Greve, et al., (*J. Mol. Appl. Genet.* (1982) 1:499–512). The EcoRI cleavage site is at position 13639, downstream from the mRNA start site. The 141 bp EcoRI-BamHI fragment of I-4, containing the cut-down promoter, is cloned into EcoRI-BamHI digested pBR322 to create pCGN428. The 141 bp EcoRI-BamHI promoter piece from pCGN428, and the 2.5 kb EcoRI-BamHI ocs5' piece from pCGN429 are cloned together into EcoRI digested pUC19 (Vieira and Messing, supra) to generate pCGN442, reconstructing the ocs upstream region with a cut-down promoter section.

To generate the ocs3' end, the HindIII fragment of pLB41 (D. Figurski, UC San Diego) containing the gentamycin resistance gene is cloned into HindIII digested pACYC184 (Chang and Cohen, supra) to create pCGN413b. The 4.7 kb BamHI fragment of pTiA6 (supra), containing the ocs3' region, is cloned into BamHI digested pBR325 (F. Bolivar, *Gene* (1978) 4:121–136) to create 33c-19. The SmaI site at position 11207 (Barker, supra) of 33c-19 is converted to an XhoI site using a synthetic XhoI linker, generating pCCG401.2. The 3.8 kb BamHI-EcoRI fragment of pCGN401.2 is cloned into BamHI-EcoRI digested pCGN413b to create pCGN419.

The ocs5'-ocs3' cassette is generated by cloning the 2.64 kb EcoRI fragment of pCGN442, containing the 5' region, into EcoRI digested pCGN419 to create pCNG446. The 3.1 kb XhoI fragment of pCGN446, having the ocs5' region (bp 13639–15208) and ocs3' region (bp 11207–12823), is cloned into the XhoI site of pCGN426 to create pCGN451.

Example 8

In this example, the preparation of a Bce-4 expression cassette containing safflower stearoyl-ACP desaturase is described.

The desaturase cDNA clone from pCGN2754 prepared as described in Example 5, is modified by in vitro mutagenesis to insert restriction sites immediately upstream of the ATG start codon and downstream of the TGA stop codon. A single-stranded template DNA is prepared for the mutagenesis reaction from pCGN1849 (described in Example 6) as described by Messing, (*Methods in Enzymol.* (1983) 101:20–79). Synthetic oligonucleotides are synthesized on an Applied Biosystems 380A DNA synthesizer. The oligonucleotides used are

5'-CCATTTTTGATCTTCCTCGAGCCCGGGCTGCA-GTTCTTCTTCTTCTTG-3' for the 5'mutagenesis and

5'-GCTCGTTTTTTTTTTCTCTGCAGCCCGGGCTC-GAGTCACAGCTTCACC -3' for the 3'-mutagenesis; both add PstI, SmaI and XhoI sites flanking the coding region. Both oligonucleotides are 5'-phosphorylated (BRL 5'-Terminus labelling kit) and used for mutagenesis with the pCGN3201 template by the procedure of Adelman et al. (*DNA* (1983) 2:183–193). The XhoI fragment from the resulting clone can be subcloned into the Bce4 expression cassette, pCGN1870 (described below) at the unique XhoI site. This Bce4/desaturase expression cassette can then be inserted in a suitable binary vector, transformed into *Agrobacterium tumefaciens* strain EHA101 and used to transform plants as provided in Example 10.

Bce-4 Expression Cassette pCGN1870 is a Bce-4 expression cassette containing 5' and 3' regulatory regions of the Bce-4 gene and may be derived from the Bce-4 sequence found in pCGN1857, which was deposited with the ATCC on Mar. 9, 1990, and assigned accession number 68251, or by methods known to one skilled in the art from the sequence provided in FIG. 5. The Bce 4 gene may be isolated as follows:

The ClaI fragment of pCGN1857, containing the Bce4 gene is ligated into ClaI digested Bluescript KS+ (Stratagene; La Jolla, Calif.), producing pCGN1864. Single stranded DNA is made from pCGN1864 and altered by in vitro mutagenesis using the oligonucleotides BCE45P:
(5'GAGTAGTGAACTTCATGGATCCTCGAGGTC-TTGAAAACCTAGA3') and BCE43P:
(5'CAATGTCTTGAGAGATCCCGGGATCCTTAA-CAACTAGGAAAAGG3') as described by Adelman et al. (*DNA* (1983) 2:183–193). The oligonucleotide BSCP2 (5'GTAAGACACGACTTATCGCCACTG3'), complementary to a portion of Bluescript, is included in the reaction to improve the yield of double-stranded DNA molecules. The resulting plasmid, pCGN1866, contains XhoI and BamHI sites (from BCE45P) immediately 5' to the Bce4 start codon and BamHI and SmaI sites (from BCE43P) immediately 3' to the Bce4 stop codon. The ClaI fragment of pCGN1866, containing the mutagenized sequences, is inserted into the ClaI site of pCGN2016 (described in Example 8), producing pCGN1866C. The ClaI fragment of pCGN1866C is used to replace the corresponding wild-type ClaI fragment of PCGN1867 (described below) to produce pCGN1868. Bce4 coding sequences are removed by digestion of pCGN1868 with BamHI and recircularization of the plasmid to produce pCGN1870. The Bce4 expression cassette, pCGN1870, contains 7.4 kb of 5' regulatory sequence and 1.9 kb of 3' regulatory sequence derived from the Bce4 genomic clone separated by the cloning sites, XhoI, BamHI;, and SmaI.

pCGN1867

The BamHI and SmaI sites of pUC18 are removed by BamHI-SmaI digestion and recircularizing of the plasmid, without repair of the ends, to produce pCGN1862 The PstI fragment of pCGN1857, containing the Bce4 gene, is inserted into the PstI site of pCGN1862 to produce pCGN1867.

Example 9

In this example, the preparation of a napin 1-2 expression cassette containing safflower stearoyl-ACP desaturase is described.

The desaturase cDNA clone from pCGN2754 is prepared and modified as described in Example 8. The XhoI fragment from the resulting clone can be subcloned into the napin 1-2 expression cassette, pCGN1808 (described below) at the unique XhoI site. This napin 1-2/desaturase expression cassette can then be inserted into a suitable binary vector, transformed into *A. tumefaciens* strain EHA101 in a like manner as described in Example 8.

Napin 1-2 Expression Cassette

An expression cassette utilizing 5' upstream sequences and 3' downstream sequences obtainable from *B. campestris* napin gene can be constructed as follows.

A 2.7 kb XhoI fragment of napin 1-2 (FIG. 7) containing 5' upstream sequences is subcloned into pCGN789 (a pUC based vector the same as pUC119 with the normal polylinker replaced by the synthetic linker—5' GGAATTCGTCGACAGATCTCTGCAGCTCGAGGGATCCAAGCTT 3' (which represented the polylinker EcoRI, SalI, BglII, PstI, XhoI, BamHI, HindIII) and results in pCGN940. The majority of the napin coding region of pCGN940 was deleted by digestion with SalI and religation to form pCGN1800. Single-stranded DNA from pCGN1800 was used in an in vitro mutagenesis reaction (Adelman et al., *DNA* (1983) 2:183–193) using the synthetic oligonucleotide 5' GCTTGTTCGCCATGGATATCTTCTGTATGTTC 3'. This oligonucleotide inserted an EcoRV and an NcoI restriction site at the junction of the promoter region and the ATG start codon of the napin gene. An appropriate mutant was identified by hybridization to the oligonucleotide used for the mutagenesis and sequence analysis and named pCGN1801.

A 1.7 kb promoter fragment was subcloned from pCGN1801 by partial digestion with EcoRV and ligation to pCGN786 (a pCGN566 chloramphenicol based vector with the synthetic linker described above in place of the normal polylinker) cut with EcoRI and blunted by filling in with DNA Polymerase I Klenow fragment to create pCGN1802.

A 2.1 kb SalI fragment of napin 1-2 (FIG. 7) containing 3' downstream sequences is subcloned into pCGN789 (described above) and results in pCGN941. pCGN941 is digested with XhoI and HindIII and the resulting approximately 1.6 kb of napin 3' sequences are inserted into XhoI-HindIII digested pCGN1802 to result in pCGN1803. In order to remove a 326 nucleotide HindIII fragment inserted opposite to its natural orientation, as a result of the fact that there are 2 HindIII sites in pCGN1803, the pCGN1803 is digested with HindIII and religated. Following religation, a clone is selected which now contains only 1.25 kb of the original 1.6 napin 3' sequence. This clone, pCGN1808 is the napin 1-2 expression cassette and contains 1.725 kb of napin promoter sequences and 1.265 kb of napin 3' sequence with the unique cloning sites SalI, BglI, PstI and XhoI in between.

Example 10

In this example, a protocol for transforming *Brassica napus* is provided.

Plant Material and Transformation

Seeds of *Brassica napus* cv. Delta are soaked in 95% ethanol for 2 min, surface sterilized in a 1.0% solution of sodium hypochlorite containing a drop of Tween 20 for 45 min., and rinsed three times in sterile, distilled water. Seeds are then plated in Magenta boxes with 1/10th concentration of Murashige minimal organics medium (Gibco) supplemented with pyriodoxine (50 $\mu$g/l), nicotinic acid (50 $\mu$g/l), glycine (200 $\mu$g/l), and 0.6% Phytagar (Gibco) pH 5.8. Seeds are germinated in a culture room at 22° C. in a 16 h photoperiod with cool fluorescent and red light of intensity approximately 65 $\mu$ Einsteins per square meter per second ($\mu$Em$^{-2}$S$^{-1}$)

Hypocotyls are excised from 7 day old seedlings, cut into pieces approximately 4 mm in length, and plated on feeder plates (Horsch et al. 1985). Feeder plates are prepared one day before use by plating 1.0 ml of a tobacco suspension culture onto a petri plate (100×25 mm) containing about 30 ml MS salt base (Carolina Biological) 100 mg/l inositol, 1.3 mg/l thiamine-HCl, 200 mg KH$_2$PO$_4$ with 3% sucrose, 2,4-D (1.0 mg/l), 0.6% Phytagar, and pH adjusted to 5.8 prior to autoclaving (MS0/1/0 medium). A sterile filter paper disc (Whatman 3 mm) is placed on top of the feeder layer prior to use. Tobacco suspension cultures are subcultured weekly by transfer of 10 ml of culture into 100 ml fresh MS medium as described for the feeder plates with 2,4-D (0.2 mg/l), Kinetin (0.1 mg/l). All hypocotyl explants are preincubated on feeder plates for 24 h. at 22° C. in continuous light of intensity 30 $\mu$Em$^{-2}$S$^{-1}$ to 65 $\mu$Em$^{-2}$S$^{-1}$.

Single colonies of *A. tumefaciens* strain EHA101 containing a binary plasmid are transferred to 5 ml MG/L broth and grown overnight at 30° C. Per liter MG/L broth contains 5 g mannitol, 1 g L-Glutamic acid or 1.15 g sodium glutamate, 0.25 g kH$_2$PO$_4$, 0.10 g NaCl, 0.10 g MGSO$_4$.7H$_2$O, 1 mg biotin, 5 g tryptone, and 2.5 g yeast extract, and the broth is adjusted to pH 7.0. Hypocotyl explants are immersed in 7–12 ml MG/L broth with bacteria diluted to 1×10$^8$ bacteria/ml and after 10–20 min. are placed onto feeder plates. After 48 h of co-incubation with Agrobacterium, the hypocotyl explants are transferred to B5 0/1/0 callus induction medium which contains filter sterilized carbenicillin (500 mg/l, added after autoclaving) and kanamycin sulfate (Boehringer Mannheim) at concentrations of 25 mg/l.

After 3–7 days in culture at 65 $\mu$Em$^{-2}$S$^{-1}$ to 75 $\mu$Em$^{-2}$S$^{-1}$ continuous light, callus tissue is visible on the cut surface and the hypocotyl explants are transferred to shoot induction medium, B5BZ (B5 salts and vitamins supplemented with 3 mg/l benzylaminopurine, 1 mg/l zeatin, 1% sucrose, 0.6% Phytagar and pH adjusted to 5.8). This medium also contains carbenicillin (500 mg/l) and kanamycin sulfate (25 mg/l). Hypocotyl explants are subcultured onto fresh shoot induction medium every two weeks.

Shoots regenerate from the hypocotyl calli after one to three months. Green shoots at least 1 cm tall are excised from the calli and placed on medium containing B5 salts and vitamins, 1% sucrose, carbenicillin (300 mg/l), kanamycin sulfate (50 mg/l) and 0.6% Phytagar) and placed in a culture room with conditions as described for seed germination. After 2–4 weeks shoots which remain green are cut at the base and transferred to Magenta boxes containing root induction medium (B5 salts and vitamins, 1% sucrose, 2 mg/l indolebutyric acid, 50 mg/l kanamycin sulfate and 0.6% Phytagar). Green rooted shoots are tested for NPT II activity.

As seen from the above results, purified plant stearoyl-ACP desaturase is provided and used to obtain nucleic acid sequences. And, in accordance with the above-invention DNA constructs may be prepared to express safflower stearoyl-ACP desaturase.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claim.

What is claimed is:

1. A recombinant DNA construct comprising the following four components operably joined in the 5' to 3' direction of transcription: a transcription initiation region functional in a host cell, a translation initiation region functional in said host cell, a DNA sequence encoding a plant stearoyl-ACP desaturase whose amino acid sequence is set forth in FIG. 2, and a transcription termination region functional in said host cell, wherein said DNA sequence encoding a plant stearoyl-ACP desaturase is in a sense orientation and wherein (a) at least one of said four components of said construct is heterologous to another one of said four components of said construct or (b) said construct further comprises an additional component which is heterologous to one of said four components of said construct.

2. A recombinant DNA construct comprising, the following components operably joined in the 5' to 3' direction of transcription: a transcription initiation control region capable of promoting transcription in a plant cell, a DNA sequence encoding a plant stearoyl-ACP desaturase whose amino acid sequence is set forth in FIG. 2, and a transcription termination region functional in a plant cell, wherein said DNA sequence encoding a plant stearoyl-ACP desaturase is in an anti-sense orientation.

3. The DNA construct of claim 1 wherein said host cell is prokaryotic.

4. The DNA construct of claim 1 wherein said host cell is eukaryotic.

5. The DNA construct of claim 2 wherein said transcription initiation region is from a gene preferentially expressed in plant embryo tissue.

6. A Brassica plant comprised of cells, said cells comprising a DNA construct according to claim 1 or 2.

7. Seed produced from a plant according to claim 6, wherein said seed contains said cells comprising a DNA construct.

8. The construct of claim 1, wherein said additional component of (b) is selected from the group consisting of a T-DNA border sequence, a marker useful for the selection of transformed cells, and a linker DNA sequence.

9. The DNA construct of claim 1 wherein said transcription initiation region is from a gene preferentially expressed in plant embryo tissue.

10. The DNA construct of claim 5 wherein said structural gene preferentially expressed in plant embryo tissue is selected from the group consisting of Bce4, seed acyl carrier protein and napkin.

11. A plant cell comprising a DNA construct according to claim 1 or claim 2 wherein said plant cell and said plant stearoyl-ACP desaturase are from the same species.

12. A plant or plant part comprised of cells, said cells comprising a DNA construct according to claim 1 or claim 2 wherein said plant stearoyl-ACP desaturase is from the same species as said plant or plant part.

13. A plant seed comprised of cells, said cells comprising a DNA construct according to claim claim 1 or claim 2.

14. The plant seed of claim 13, wherein said plant is Brassica.

15. A plant seed comprised of cells, said cells comprising a DNA construct according to any one of claims 2 or 11 wherein said plant stearoyl-ACP desaturase is from the same species as said plant or plant part.

16. The plant seed of claim 15, wherein said plant is Brassica.

17. The DNA construct of claim 9 wherein said transcription initiation region is from a gene preferentially expressed in plant embryo tissue is selected from the group consisting of Bce4, seed acyl carrier protein and napin.

18. A cDNA sequence encoding a plant stearoyl-ACP desaturase, wherein said cDNA sequence encodes the safflower stearoyl-ACP desaturase whose amino acid sequence is set forth in FIG. 2.

19. A plant cell comprising:

a recombinant DNA construct according to claim 1 or claim 2.

20. A plant or plant part comprising:

cells, said cells comprising a recombinant DNA construct according to claim 1 or claim 2.

21. A cell comprising:

a recombinant DNA construct according to claim 1 or claim 2.

22. A plant cell comprising a recombinant DNA construct comprising as components transcriptional and translational initiation and termination regions functional in said plant or plant part operably linked to a DNA sequence encoding a plant Δ-9 desaturase protein having any one of the amino acid peptide sequences shown in FIG. 1. F1–7 and F9–11 wherein at least one of said components of said DNA construct is heterologous to another one of said four components of said construct or said construct further comprises an additional component which is heterologous to one of said components of said construct.

23. A plant or plant part comprised of cells, said cells comprising a recombinant DNA construct comprising as components transcriptional and translational initiation and termination regions functional in said plant or plant part operably linked to a DNA sequence encoding a plant Δ-9 desaturase protein having any one of the amino acid peptide sequences shown in FIG. 1. F1–7, and F9–11 wherein at least one of said components of said DNA construct is heterologous to another one of said four components of said construct or said construct further comprises an additional component which is heterologous to one of said components of said construct.

24. A cell comprising a recombinant DNA construct comprising as components transcriptional and translational initiation and termination regions functional in said plant or plant part operably linked to a DNA sequence encoding a Δ-9 plant desaturase protein having any one of the amino acid peptide sequences shown in FIG. 1. F1–7 and F9–11 wherein at least one of said components of said DNA construct is heterologous to another one of said components of said construct or said construct further comprises an additional component which is heterologous to one of said components of said construct.

25. The plant cell according to claim 22, wherein amino acid peptide is KEIPDDYFVVLVGDMITEEALPTYQTMLNT (underlined amino acids of FIG. 1, F2).

26. The plant cell according to claim 22, wherein said DNA sequence encodes the amino acid peptide DYADILEFLVGRWK (FIG. 1, F10).

27. The plant or plant part comprised of cells according to claim 23, wherein said DNA sequence encodes the amino acid peptide KEIPDDYFVVLVGMITEEALPTYQTMLNT (underlined amino acids of FIG. 1, F2).

28. The plant or plant part comprised of cells according to claim 23, wherein said DNA sequence encodes the amino acid peptide DYADILEFLVGRWK (SEQ ID NO: 10).

29. The cell according to claim 24, wherein said DNA sequence encodes the amino acid peptide KEIPDDYFVVLVGDMITEEALPTYQTMLNT (underlined amino acids of FIG. 1, F2).

30. The cell according to claim 24, wherein said DNA sequence encodes the amino acid peptide DYADILEFLVGRWK (FIG. 1, F10).

* * * * *